(12) United States Patent
Caligiuri et al.

(10) Patent No.: US 10,167,311 B2
(45) Date of Patent: Jan. 1, 2019

(54) BORONIC ACID ESTERS AND PHARMACEUTICAL FORMULATIONS THEREOF

(71) Applicant: OHIO STATE INNOVATION FOUNDATION, Columbus, OH (US)

(72) Inventors: Michael Caligiuri, Columbus, OH (US); Robert Lee, Columbus, OH (US); Guido Marcucci, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/116,312

(22) PCT Filed: Feb. 3, 2015

(86) PCT No.: PCT/US2015/014263
§ 371 (c)(1),
(2) Date: Aug. 3, 2016

(87) PCT Pub. No.: WO2015/117136
PCT Pub. Date: Aug. 6, 2015

(65) Prior Publication Data
US 2016/0347791 A1 Dec. 1, 2016

Related U.S. Application Data

(60) Provisional application No. 61/935,040, filed on Feb. 3, 2014, provisional application No. 62/036,876, filed on Aug. 13, 2014.

(51) Int. Cl.
*C07K 5/06* (2006.01)
*A61K 38/05* (2006.01)
(Continued)

(52) U.S. Cl.
CPC .......... *C07K 5/06191* (2013.01); *A61K 9/127* (2013.01); *A61K 38/05* (2013.01);
(Continued)

(58) Field of Classification Search
CPC .............. A61K 47/48046; A61K 9/127; A61K 47/48053; A61K 38/05; C07K 5/06191; C07F 5/04
(Continued)

(56) References Cited

U.S. PATENT DOCUMENTS

| | | |
|---|---|---|
| 4,499,082 A | 2/1985 | Shenvi et al. |
| 5,106,948 A | 4/1992 | Kinder et al. |

(Continued)

FOREIGN PATENT DOCUMENTS

| | | |
|---|---|---|
| WO | 98/35691 A1 | 8/1998 |
| WO | 99/15183 A1 | 4/1999 |

(Continued)

OTHER PUBLICATIONS

Zhu; J. Med. Chem. 2009, 52, 4192-4199.*
(Continued)

*Primary Examiner* — Daniel R Carcanague
(74) *Attorney, Agent, or Firm* — Meunier Carlin & Curfman LLC

(57) ABSTRACT

Provided herein are boronic acid esters of boronic acid therapeutic agents, such as bortezomib. The boronic acid esters can be used to prepare liposomal formulations of boronic acid therapeutic agents with improved properties, such as enhanced stability. This disclosure, in one aspect, relates to compositions and methods of making and using the compositions.

13 Claims, 8 Drawing Sheets

(51) Int. Cl.
*A61K 9/127* (2006.01)
*C07F 5/04* (2006.01)
*A61K 47/54* (2017.01)

(52) U.S. Cl.
CPC .......... *A61K 47/543* (2017.08); *A61K 47/544* (2017.08); *C07F 5/04* (2013.01)

(58) Field of Classification Search
USPC ........................................................ 549/213
See application file for complete search history.

(56) References Cited

U.S. PATENT DOCUMENTS

| | | |
|---|---|---|
| 5,169,841 A | 12/1992 | Kleeman et al. |
| 5,187,157 A | 2/1993 | Kettner et al. |
| 5,242,904 A | 9/1993 | Kettner et al. |
| 5,250,720 A | 10/1993 | Kettner et al. |
| 5,574,014 A | 11/1996 | Claeson et al. |
| 5,780,454 A | 7/1998 | Adams et al. |
| 5,856,306 A | 1/1999 | Claeson et al. |
| 6,066,730 A | 5/2000 | Adams et al. |
| 6,083,903 A | 7/2000 | Adams et al. |
| 6,114,308 A | 9/2000 | Claeson et al. |
| 6,297,217 B1 | 10/2001 | Adams et al. |
| 6,465,433 B1 | 10/2002 | Adams et al. |
| 6,548,668 B2 | 4/2003 | Adams et al. |
| 6,617,317 B1 | 9/2003 | Adams et al. |
| 6,713,446 B2 | 3/2004 | Gupta |
| 6,747,150 B2 | 6/2004 | Adams et al. |
| 6,958,319 B2 | 10/2005 | Gupta |
| 7,119,080 B2 | 10/2006 | Adams et al. |
| 7,531,526 B2 | 5/2009 | Adams et al. |
| 8,003,791 B2 | 8/2011 | Adams et al. |
| 8,263,578 B2 | 9/2012 | Soppimath et al. |
| 8,378,099 B2 | 2/2013 | Adams et al. |
| 2002/0169114 A1 | 11/2002 | Gupta |
| 2006/0153907 A1 | 7/2006 | Zalipsky et al. |
| 2006/0159736 A1 | 7/2006 | Zalipsky et al. |
| 2007/0053845 A1 | 3/2007 | Sengupta et al. |
| 2009/0092661 A1 | 4/2009 | Huang et al. |
| 2009/0092662 A1 | 4/2009 | Huang et al. |
| 2010/0174072 A1 | 7/2010 | Pickersgill et al. |
| 2010/0247669 A1 | 9/2010 | Eliasof et al. |
| 2010/0272822 A1 | 10/2010 | Sengupta et al. |
| 2011/0082108 A1 | 4/2011 | Bachovchin |
| 2011/0158983 A1 | 6/2011 | Bascomb et al. |
| 2011/0178470 A1 | 7/2011 | Kocherlakota et al. |
| 2011/0230441 A1 | 9/2011 | Soppimath et al. |
| 2012/0172808 A1* | 7/2012 | Soppimath .......... A61K 9/0019 604/187 |
| 2012/0322762 A1 | 12/2012 | Soppimath et al. |
| 2012/0322763 A1 | 12/2012 | Soppimath et al. |
| 2013/0171091 A1 | 7/2013 | Sengupta et al. |
| 2013/0310320 A1 | 11/2013 | Adams et al. |

FOREIGN PATENT DOCUMENTS

| | | |
|---|---|---|
| WO | 02/059131 A1 | 8/2002 |
| WO | 2006052733 A2 | 2/2009 |
| WO | 2009026427 A2 | 2/2009 |
| WO | 2009026430 A2 | 2/2009 |
| WO | 2009/154737 A1 | 12/2009 |
| WO | 2011116286 A2 | 9/2011 |
| WO | 2012073125 A1 | 6/2012 |
| WO | WO 2014/121291 * | 8/2014 |

OTHER PUBLICATIONS

International Search Report and Written Opinion of the International Searching Authority for PCT/US2015/014263, dated May 7, 2015, 9 pages.
European Search Report, issued by the European Patent Office in Application No. 15742988.7, dated May 30, 2017, 7 pages.
Communication Pursuant to Article 94(3) EPC, issued by the European Patent Office in Application No. 15742988.7, dated Jun. 19, 2017, 5 pages.

* cited by examiner

BORONIC ACID ESTERS AND PHARMACEUTICAL FORMULATIONS THEREOF

CROSS-REFERENCE TO RELATED APPLICATIONS

This application claims benefit of U.S. Provisional Application No. 61/935,040, filed Feb. 3, 2014, and U.S. Provisional Application No. 62/036,876, filed Aug. 13, 2014, both of which are hereby incorporated herein by reference in their entirety.

STATEMENT REGARDING FEDERALLY SPONSORED RESEARCH OR DEVELOPMENT

This invention was made with Government Support under Grant No. R01CA149623-01A1 awarded by the National Institutes of Health. The Government has certain rights in the invention.

BACKGROUND

Boronic acid compounds display a variety of pharmaceutically useful biological activities. Shenvi et al., U.S. Pat. No. 4,499,082 discloses that peptide boronic acids are inhibitors of certain proteolytic enzymes. Kettner and Shenvi, U.S. Pat. No. 5,187,157; U.S. Pat. No. 5,242,904; and U.S. Pat. No. 5,250,720, disclose a class of peptide boronic acids that inhibit trypsin-like proteases. Kleetnan et al., U.S. Pat. No. 5,169,841, discloses N-terminally modified peptide boronic acids that inhibit the action of renin. Kinder et al., U.S. Pat. No. 5,106,948, discloses that certain tripeptide boronic acid compounds inhibit the growth of cancer cells.

Adams et al., U.S. Pat. No. 5,780,454, U.S. Pat. No. 6,066,730, U.S. Pat. No. 6,083,903, and U.S. Pat. No. 6,297,217, hereby incorporated by reference in their entirety for their disclosure of boronic ester and acid compounds, disclose peptide boronic ester and acid compounds useful as proteasome inhibitors. The references also describe the use of boronic ester and acid compounds to reduce the rate of muscle protein degradation, to reduce the activity of NF-κB in a cell, to reduce the rate of degradation of p53 protein in a cell, to inhibit cyclin degradation in a cell, to inhibit the growth of a cancer cell, to inhibit antigen presentation in a cell, to inhibit NF-κB dependent cell adhesion, and to inhibit HIV replication. Brand et al., WO 98/35691, discloses that proteasome inhibitors, including boronic acid compounds, are useful for treating infarcts such as those that occur during stroke or myocardial infarction. Elliott et al., WO 99/15183, discloses that proteasome inhibitors are useful for treating inflammatory and autoimmune diseases.

Bortezomib (BTZ) is a boronic acid proteasome inhibitor currently approved by the U.S. Food and Drug Administration for the treatment of multiple myeloma and mantle cell lymphoma. BTZ is administered clinically by either subcutaneous or intravenous injection. While treatment with BTZ can be effective, administration of free BTZ is plagued by high toxicity, non-specific tissue uptake, side effects, and rapid clearance from circulation. BTZ also possesses limited stability (e.g., a limited shelf complicating the therapeutic use of BTZ. Efforts have been made to develop improved BTZ formulations that address these shortcomings.

Liposomes are spherical vesicles made of a lipid bilayer (e.g., a phospholipid bilayer) that are capable of encapsulating hydrophilic drugs in their aqueous core or hydrophobic drugs within their lipid bilayer. Liposomal drugs can provide prolonged systemic circulation time, decreased drug toxicity, and enhanced drug delivery efficacy. For example, liposomal formulations of certain chemotherapeutics, including daunorubicin (sold under the name DAUNOXOME by Gilead Sciences), doxorubicin (sold under the name DOXIL by Ortho Biotech and under the name CAELYX by Schering-Plough), and vincristine (sold under the name MARQIBO by Spectrum Pharmaceuticals), have been approved by the FDA and exhibit prolonged systemic circulation time, decreased drug toxicity, and enhanced drug delivery efficacy relative to alternative formulations of these chemotherapeutics.

Efforts to prepare liposomal formulations of boronic acid and ester compounds, such as BTZ, have thus far suffered from significant drawbacks. Passive entrapment methods and remote loading methods have both been used to prepare liposomal formulations of BTZ. Passive entrapment methods provide a very low encapsulation efficacy, usually lower than 15%, which is problematic. To address this issue, remote loading was developed in which the entrapment of BTZ in pre-formed liposomes is driven by a pH and chemical gradient. This process is complex and requires overnight incubation. In addition, the stability of the resulting liposomes is poor, which can preclude clinical development.

In order to further increase the shelf-life of liposomes, lyophilization has been utilized. However, as both the passive entrapment and remote loading processes entrap the drug in the aqueous core of the liposome, the contents of the liposome tend to leak out during dehydration and rehydration processes, even in the presence of a lyoprotectant.

New formulations of boronic acid active agents, such as BTZ, that exhibit improved properties, such as enhanced stability, are needed to address these shortcomings. The compositions and methods disclosed herein address these and other needs.

SUMMARY

In accordance with the purposes of the disclosed subject matter, as embodied and broadly described herein, this disclosure, in one aspect, relates to compositions and methods of making and using the compositions. In further examples, the subject matter disclosed herein relates to boronic acid esters of boronic acid therapeutic agents. The boronic acid esters can be used to prepare liposomal formulations that contain and/or release boronic acid therapeutic agents with improved properties, such as enhanced stability.

For example, disclosed herein are compounds of Formula I

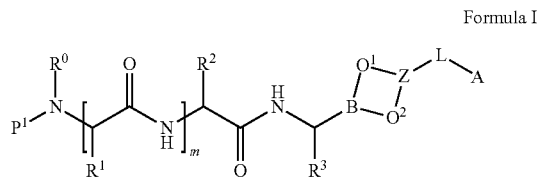

Formula I wherein $P^1$ can be hydrogen or an amino-group protecting moiety;

$R^0$ can be hydrogen or an alkyl group;

$R^1$, $R^2$, and $R^3$ can be independently hydrogen, an alkyl group, a cycloalkyl group, a heterocyclyl group, an aryl group, a heteroaryl group, or $-CH_2-R^4$;

R[4] can be an aryl group, an alkylaryl group, an arylalkyl group, a cycloalkyl group, an alkylcycloalkyl group, a heterocyclyl group, an alkylheterocyclyl group, a heteroaryl group, an alkylheteroaryl group, an alkoxy group, or an alkylthio group;

m can be 0, 1, or 2;

Z, together with $O^1$ and $O^2$, represent a moiety derived from a polyol;

L can be absent or a linking group; and

A can be a lipophilic moiety.

In some examples, m is 0.

In some examples, $P^1$ can be an amino-group protecting moiety. For example, $P^1$ can be $R^5$—C(O)—, $R^5$—S(O)$_2$—, $R^5$—NH—C(O)—, or $R^5$—O—C(O)—, where $R^5$ is an alkyl group, an aryl group, an alkylaryl group, an arylalkyl group, a cycloalkyl group, an alkylcycloalkyl group, a heterocyclyl group, an alkylheterocyclyl group, a heteroaryl group, or an alkylheteroaryl group. In some examples, $P^1$ can be $R^5$—C(O)—, $R^5$—S(O)$_2$—, $R^5$—NH—C(O)—, or $R^5$—O—C(O)—, and $R^5$ is a heteroaryl group. In certain examples, $P^1$ can be (2-pyrazine)carbonyl.

In certain examples, $R^3$ is an isobutyl group.

The polyol can be any suitable polyol. In some examples, the polyol can comprise a sugar (e.g., a monosaccharide such as fructose). In certain examples, the polyol can comprise a reduced sugar (e.g., a sugar alcohol such as mannitol, sorbitol, or galactitol). In certain examples, the polyol can comprise an amino sugar (e.g., meglumine or glucamine). In certain examples, the polyol can be meglumine, glucamine, mannitol, sorbitol, or fructose.

A can be any suitable lipophilic moiety. The lipophilic moiety can be derived from a lipid. In some examples, the lipid can comprise a fatty acid, a glycerolipid, a phospholipid, a sphingolipid, a sterol, or a prenol.

In some examples, A can be a $C_8$-$C_{40}$ alkyl group, a $C_8$-$C_{40}$ alkenyl group, a $C_8$-$C_{40}$ alkoxy group, a $C_8$-$C_{40}$ alkylthio group, a $C_8$-$C_{40}$ alkylsulfinyl group, a $C_8$-$C_{40}$ alkylsulfonyl group, a $C_8$-$C_{40}$ alkylamino group, a $C_8$-$C_{40}$ dialkylamino group, a $C_8$-$C_{40}$ alkylcarbonyl group, a $C_8$-$C_{40}$ alkoxycarbonyl group, a $C_8$-$C_{40}$ alkylaminocarbonyl group, a $C_8$-$C_{40}$ dialkylaminocarbonyl group, or a moiety defined by the formula

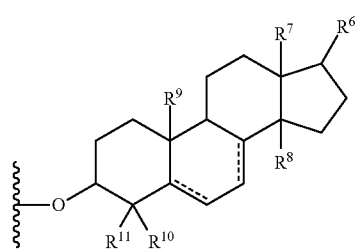

wherein the dotted lines indicate that a single or double bond is present;

$R^6$ can be an alkyl group, an alkenyl group, an alkynyl group, an aryl group, an alkylaryl group, an arylalkyl group, a cycloalkyl group, an alkylcycloalkyl group, a heterocyclyl group, an alkyheterocyclyl group, a heteroaryl group, an alkylheteroaryl group, an alkoxy group, or an alkylthio group; and $R^7$, $R^8$, $R^9$, $R^{10}$, and $R^{11}$ can be, independently, hydrogen, a hydroxy group, an amino group, an alkyl group, an alkenyl group, an alkynyl group, an aryl group, an alkylaryl group, an arylalkyl group, a cycloalkyl group, an alkylcycloalkyl group, a heterocyclyl group, an alkylheterocyclyl group, a heteroaryl group, an alkylheteroaryl group, an alkoxy group, an alkylthio group, an alkylsulfinyl group, an alkylsulfonyl group, an alkylamino group, a dialkylamino group, an alkylcarbonyl group, an alkoxycarbonyl group, an alklaminocarbonyl group, or a dialkylaminocarbonyl group.

In certain examples, the compound can be defined by Formula IA

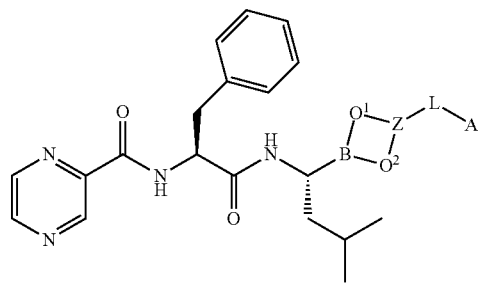

Formula IA where Z, L, and A can be as defined above with respect to Formula I.

In certain examples, the compound can be defined by Formula II

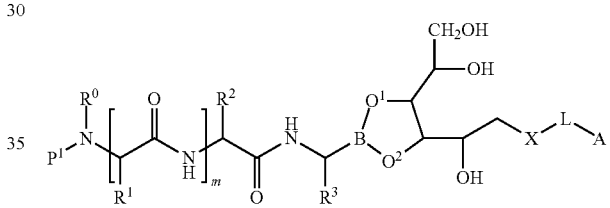

Formula II wherein $P^1$, $R^0$, $R^1$, $R^2$, $R^3$, $R^4$, m, L, and A can be as defined above with respect to Formula I, X can be —O— or —NR$^{12}$—; and $R^{12}$ can be hydrogen or an alkyl group.

In certain examples, $R^{12}$ can be hydrogen. In other examples, $R^{12}$ is an alkyl group. For example, $R^{12}$ can be a $C_1$-$C_6$ alkyl group. In some examples, $R^{12}$ can be a $C_1$-$C_4$ alkyl group. In certain examples, $R^{12}$ can be methyl or ethyl.

In certain examples, X can be —O—. In other examples, X can be —NH— or —N(CH$_3$)—.

In certain examples, the compound can be defined by Formula IIA

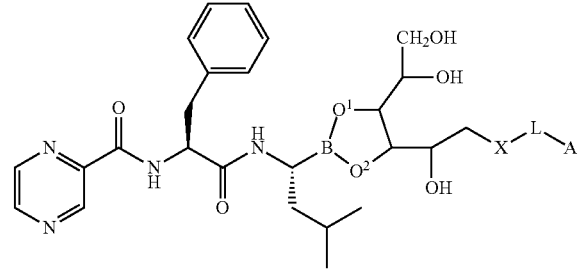

Formula IIA wherein X, $R^{12}$, L, and A can be as defined above with respect to Formula II.

In certain examples, the compound can be one of the following.
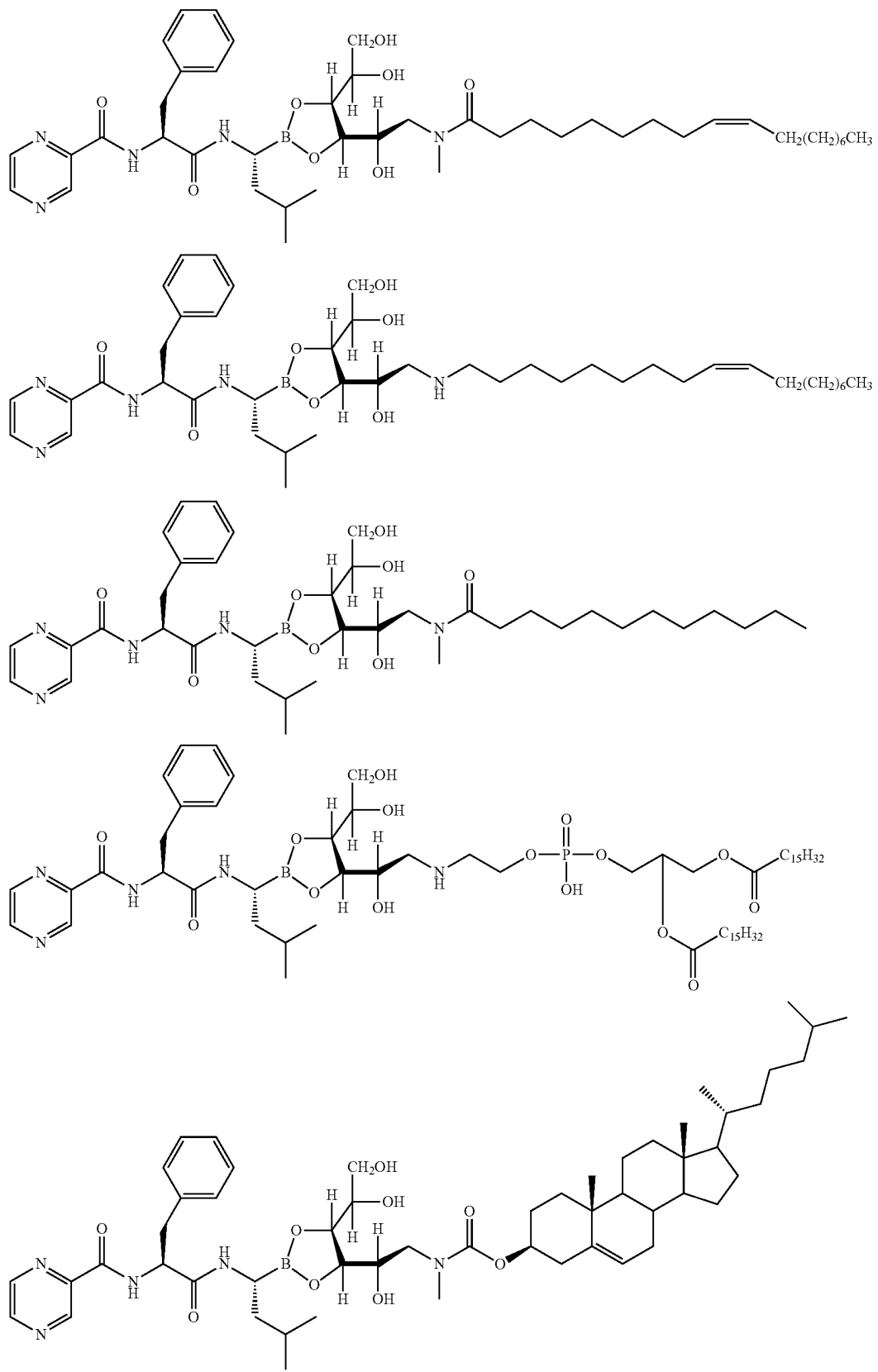

At neutral or alkaline pH (e.g., a pH of 8), the boronic esters described herein can be anionic. In these cases, an additional deprotonated hydroxyl group can be attached to the boron atom of the compounds described herein, and the compounds can exist in a salt form.

Also provided are pharmaceutical formulations that include liposomes formed from a vesicle-forming lipid, and a compound described herein entrapped in the liposomes. In some examples, the formulation can be lyophilized. The liposomal formulations can maintain stability during lyophilization, and once lyophilized, can remain stable when stored at room temperature for periods of up to six months. In some examples, the formulation can further include a lyoprotectant, such as sucrose or trehalose.

Also provided are methods of treating cancer in a subject. Methods can include administering to the subject a therapeutically effective amount of a compound or formulation described herein.

Additional advantages of the disclosed subject matter will be set forth in part in the description that follows and the Figures, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying Figures, which are incorporated in and constitute a part of this specification, illustrate several aspects described below.

DETAILED DESCRIPTION

Figure 1:
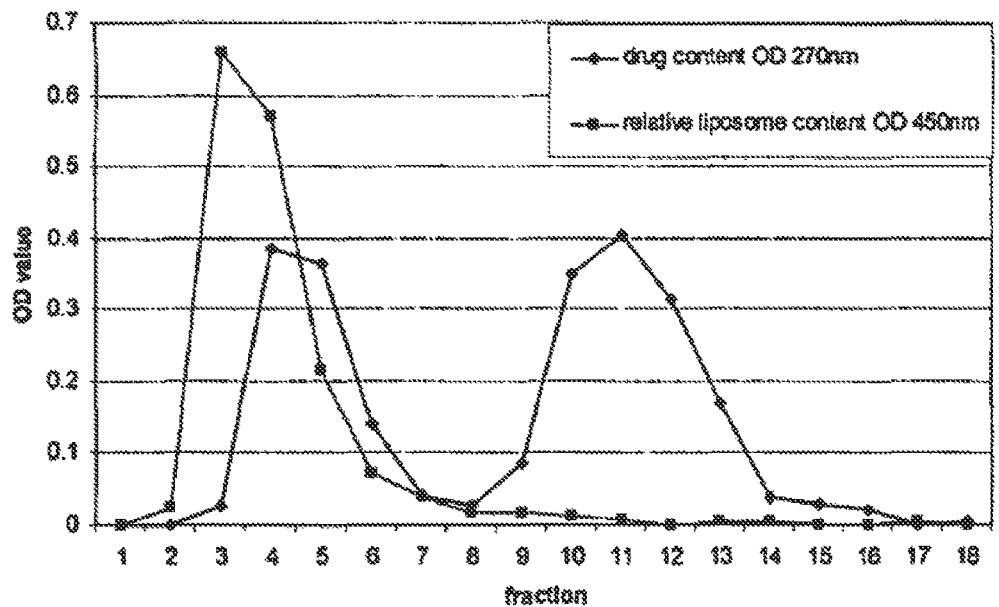
FIG. 1 is a Sepharose CL-4B chromatogram illustrating the loading of a liposomal formulation of BTZ-OMG.

The materials, compounds, compositions, articles, and methods described herein may be understood more readily by reference to the following detailed description of specific aspects of the disclosed subject matter and the Examples and Figures included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

The term "anticancer" refers to the ability to treat or control cellular proliferation and/or tumor growth at any concentration.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix $C_n$-$C_m$ indicates in each case the possible number of carbon atoms in the group.

The term "alkyl," as used herein, refers to saturated straight, branched, primary, secondary or tertiary hydrocarbons, including those having 1 to 20 atoms. In some examples, alkyl groups will include $C_1$-$C_{12}$, $C_1$-$C_{10}$, $C_1$-$C_8$, $C_1$-$C_6$, $C_1$-$C_5$, $C_1$-$C_4$, $C_1$-$C_3$, or $C_1$-$C_2$ alkyl groups. Examples of $C_1$-$C_{10}$ alkyl groups include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl groups, as well as their isomers. Examples of $C_1$-$C_4$-alkyl groups include, for example, methyl, ethyl, propyl, 1-methylethyl, butyl, 1-methylpropyl, 2-methylpropyl, and 1,1-dimethylethyl groups.

Cyclic alkyl groups or "cycloalkyl" groups include cycloalkyl groups having from 3 to 10 carbon atoms. Cycloalkyl groups can include a single ring, or multiple condensed rings. In some examples, cycloalkyl groups include $C_3$-$C_4$, $C_4$-$C_7$, $C_5$-$C_7$, $C_4$-$C_6$, or $C_5$-$C_6$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

Alkyl and cycloalkyl groups can be unsubstituted or substituted with one or more moieties chosen from alkyl, halo, haloalkyl, hydroxyl, carboxyl, acyl, acyloxy, amino, alkyl- or dialkylamino, amido, arylamino, aryloxy, nitro, cyano, azido, imino, sulfonic acid, sulfate, sulfonyl, sulfanyl, sulfamonyl, ester, phosphonyl, phosphinyl, phosphoryl, phosphine, thioester, thioether, acid halide, anhydride, oxime, hydrazine, carbamate, phosphoric acid, phosphate, phosphonate, or any other viable functional group that does not inhibit the biological activity of the compounds of the invention, either unprotected, or protected as necessary, as known to those skilled in the art, for example, as described in Greene, et al, *Protective Groups in Organic Synthesis*, John Wiley and Sons, Third Edition, 1999, hereby incorporated by reference.

Terms including the term "alkyl," such as "alkylamino" or "dialkylamino," will be understood to comprise an alkyl group as defined above linked to another functional group, where the group is linked to the compound through the last group listed, as understood by those of skill in the art.

The term "alkenyl," as used herein, refers to both straight and branched carbon chains which have at least one carbon-carbon double bond. In some examples, alkenyl groups can include $C_2$-$C_{20}$ alkenyl groups. In other examples, alkenyl can include $C_2$-$C_{12}$, $C_2$-$C_{10}$, $C_2$-$C_8$, $C_2$-$C_6$, or $C_2$-$C_4$ alkenyl groups. In one embodiment of alkenyl, the number double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups can include more than one double bond in the chain. The one or more unsaturations within the alkenyl group can be located at any position(s) within the carbon chain as valence permits. In some examples, when the alkenyl group is covalently bound to one or more additional moieties, the carbon atom(s) in the alkenyl group that are covalently bound to the one or more additional moieties are not part of a carbon-carbon double bond within the alkenyl group, Examples of alkenyl groups include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl- 2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl groups.

The term "alkynyl," as used herein, refers to both straight and branched carbon chains which have at least one carbon-carbon triple bond. In one embodiment of alkynyl, the number of triple bonds is 1-3; in another embodiment of alkynyl, the number of triple bonds is one or two. In some examples, alkynyl groups include from $C_2$-$C_{20}$ alkynyl groups. In other examples, alkynyl groups can include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl, and 4-methylpent-2-yn-5-yl groups.

Alkenyl and alkynyl groups can be unsubstituted or substituted with one or more moieties chosen from alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrazine, carbamate, phosphoric acid, phosphate, phosphonate, or any other viable functional group that does not inhibit the biological activity of the compounds of the invention, either unprotected, or protected as necessary, as known to those skilled in the art, for example, as described in Greene, et al., *Protective Groups in Organic Synthesis*, John Wiley and Sons, Third Edition, 1999.

The term "aryl," as used herein, refers to a monovalent aromatic carbocyclic group of from 6 to 14 carbon atoms. Aryl groups can include a single ring or multiple condensed rings. In some examples, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups can be unsubstituted or substituted by one or more moieties chosen from halo, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkenylsulfinyl, alkynyl-sulfinyl, haloalkylsulfinyl, haloalkenylsulfinyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl.

The term "alkylaryl," as used herein, refers to an aryl group that is bonded to a parent compound through a diradical alkylene bridge, (—$CH_2$—)$_n$, where n is 1-2 (e.g., n is from 1 to 6) and where "aryl" is as defined above. The term "arylalkyl," as used herein, refers to an aryl group, as defined above, which is substituted by an alkyl group, as defined above.

The term "alkylcycloalkyl," as used herein, refers to a cycloalkyl group that is bonded to a parent compound through a diradical alkylene bridge, (—$CH_2$—)$_n$, where n is 1-12 (e.g., n is from 1 to 6) and where "cycloalkyl" is as defined above.

The term "alkoxy," as used herein, refers to alkyl-O—, wherein alkyl refers to an alkyl group, as defined above. Similarly, the terms "alkenyloxy," "alkynyloxy," and "cycloalkoxy," refer to the groups alkenyl-O—, alkynyl-O—, and cycloalkyl-O—, respectively, wherein alkenyl, alkynyl, and cycloalkyl are as defined above. Examples of $C_1$-$C_6$-alkoxy groups include, but are not limited to, methoxy, ethoxy, $C_2H_5$—$CH_2O$—, $(CH_3)$, CHO—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethlpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, and 1-ethyl-2-methylpropoxy.

The term "alkyithio," as used herein, refers to alkyl-S—, wherein alkyl refers to an alkyl group, as defined above. Similarly, the term "cycloalkylthio," refers to cycloalkyl-S— where cycloalkyl are as defined above.

The term "alkylsulfinyl," as used herein, refers to alkyl-S(O)—, wherein alkyl refers to an alkyl group, as defined above.

The term "alkylsulfonyl," as used herein, refers to alkyl-S(O)$_2$—, wherein alkyl is as defined above.

The terms "alkylamino" and "dialkylamino," as used herein, refer to alkyl-NH— and (alkyl)$_2$N— groups, where alkyl is as defined above.

The terms "alkylcarbonyl," "alkoxycarbonyl," "alkylarainocarbonyl," and "dialkylaminocarbonyl," as used herein, refer to alkyl-C(O)—, alkoxy-C(O)—, alkylamino-C(O)— and dialkylamino-C(O)— respectively, where alkyl, alkoxy, alkylamino, and dialkylamino are as defined above.

The term "heteroaryl," as used herein, refers to a monovalent aromatic group of from 1 to 15 carbon atoms (e.g., from 1 to 10 carbon atoms, from 2 to 8 carbon atoms, from 3 to 6 carbon atoms, or from 4 to 6 carbon atoms) having one or more heteroatoms within the ring. The heteroaryl group can include from 1 to 4 heteroatoms, from 1 to 3 heteroatoms, or from 1 to 2 heteroatoms. In some examples, the heteroatom(s) incorporated into the ring are oxygen, nitrogen, sulfur, or combinations thereof. When present, the nitrogen and sulfur heteroatoms can optionally be oxidized. Heteroaryl groups can have a single ring (e.g., pyridyl or furyl) or multiple condensed rings provided that the point of attachment is through a heteroaryl ring atom. Preferred heteroaryls include pyridyl, piridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings can be unsubstituted or substituted by one or more moieties as described for aryl above.

The term "alkylheteroaryl," as used herein, refers to a heteroaryl group that is bonded to a parent compound through a diradical alkylene bridge, (—CH$_2$—)$_n$, where n is 1-12 and where "heteroaryl" is as defined above.

The terms "heterocyclyl," "heterocyclic" and "heterocyclo" are used herein interchangeably, and refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, having one or more heteroatoms within the ring. The heterocyclyl group can include from 1 to 4 heteroatoms, from 1 to 3 heteroatoms, or from 1 to 2 heteroatoms. In some examples, the heteroatom(s) incorporated into the ring are oxygen, nitrogen, sulfur, or combinations thereof. When present, the nitrogen and sulfur heteroatoms can optionally be oxidized, and the nitrogen heteroatoms can optionally be quaternized. The heterocyclyl group can be attached at any heteroatom or carbon atom of the ring or ring system and can be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazapinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrabenzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl]or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

The term "alkylheterocyclyl," as used herein, refers to a heterocyclyl group that is bonded to a parent compound through a diradical alkylene bridge, (—CH$_2$—)$_n$, where n is 1-12 and where "heterocyclyl" is as defined above. The term "heterocyclylalkyl," as used herein, refers to a heterocyclyl group, as defined above, which is substituted by an alkyl group, as defined above.

Heretrocyclyl and heteroaryl groups can be unsubstituted or substituted with one or more moieties chosen from alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrazine, carbamate, phosphoric acid, phosphate, phosphonate, or any other viable functional group that does not inhibit the biological activity of the compounds of the invention, either unprotected, or protected as necessary, as known to those skilled in the art, for example, as described in Greene, et al., *Protective Groups in Organic Synthesis*, John Wiley and Sons, Third Edition, 1999.

The term "halogen," as used herein, refers to the atoms fluorine, chlorine, bromine and iodine. The prefix halo- (e.g., as illustrated by the term haloalkyl) refers to all degrees of halogen substitution, from a single substitution to a perhalo substitution (e.g., as illustrated with methyl as chloromethyl (—CH$_2$Cl), dichloromethyl (—CHCl$_2$), trichloromethyl (—CCl$_3$)).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

Disclosed herein are boronic acid esters of boronic acid therapeutic agents. The boronic acid esters can function as prodrugs for the boronic acid therapeutic agents. The boronic acid esters can be used to prepare liposomal formulations with improved properties, such as enhanced stability.

In certain aspects, disclosed herein are compounds defined by Formula I

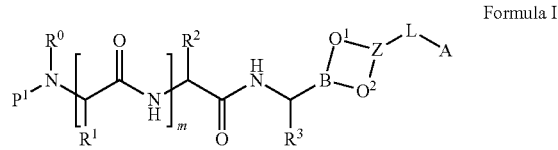

Formula I wherein

P$^1$ is hydrogen or an amino-group protecting moiety;

R$^0$ is hydrogen or an alkyl group;

R$^1$, R$^2$, and R$^3$ are independently hydrogen, an alkyl group, a cycloalkyl group, a heterocyclyl group, an aryl group, a heteroaryl group, or —CH$_2$—R$^4$;

R$^4$ is an aryl group, an allylaryl group, an arylalkyl group, a cycloalkyl group, an alkylcycloalkyl group, a heterocyclyl group, an alkylheterocyclyl group, a heteroaryl group, alkylheteroaryl group, an alkoxy group, or an alkylthio group;

m is 0, 1, or 2;

Z, together with O$^1$ and O$^2$, represent a moiety derived from a polyol;

L is absent or is a linking group; and

A is a lipophilic moiety.

In some examples, $P^1$ is an amino-group protecting moiety. Amino-group protecting moieties include groups that are used to derivatize an amino group, especially an N-terminal amino group of a peptide or amino acid. Such groups include, without limitation, alkyl, acyl, alkoxycarbonyl, aminocarbonyl, and sulfonyl moieties. However, the term "amino-group protecting moiety" is not intended to be limited to those particular protecting groups that are commonly employed in organic synthesis, nor is it intended to be limited to groups that are readily cleavable.

In some examples, $P^1$ is $R^5$—C(O)—, $R^5$—S(O)$_2$—, $R^5$—NH—C(O)—, or $R^5$—O—C(O)—, wherein $R^5$ is an alkyl group, an aryl group, an alkylaryl group, an arylalkyl group, a cycloalkyl group, an alkylcycloalkyl group, a heterocyclyl group, an alkylheterocyclyl group, a heteroaryl group, or an alkylheteroaryl group. In certain examples, $P^1$ is $R^5$—C(O)—, $R^5$—S(O)$_2$—, $R^5$—NH—C(O)—, or $R^5$—O—C(O)—, and $R^5$ is a heteroaryl group. In certain examples, $P^1$ is (2-pyrazine)carbonyl.

In some examples, $R^0$ is hydrogen. In other examples, $R^0$ is an alkyl group. For example, $R^0$ can be a $C_1$-$C_6$ alkyl group. In some examples, $R^0$ can be a $C_1$-$C_4$ alkyl group. In certain examples, $R^0$ can be methyl or ethyl.

In some examples, $R^1$, $R^2$, and $R^3$ are each independently chosen from hydrogen, $C_1$-$C_8$ alkyl, $C_3$-$C_{10}$ cycloalkyl, $C_6$-$C_{10}$ aryl, and —CH$_1$—$R^4$, wherein each of $R^1$, $R^2$, $R^3$, and $R^4$ can be optionally substituted as described above. In some examples, $R^1$, $R^2$, and $R^3$ are each independently chosen from $C_1$-$C_4$ alkyl and —CH$_2$—$R^4$, and $R^4$ is one of cycloalkyl, aryl, heterocyclyl, heteroaryl, or alkoxy. In some examples, $R^1$, $R^2$, and $R^3$ are each independently chosen from $C_1$-$C_4$ alkyl and —CH$_2$—$R^4$, and $R^4$ is one of $C_6$-$C_{10}$ aryl, ($C_6$-$C_{10}$)ar($C_1$-$C_6$)alkyl, ($C_1$-$C_6$)alk($C_6$-$C_{10}$)aryl, $C_3$-$C_{10}$ cycloalkyl, $C_1$-$C_8$ alkoxy, or $C_1$-$C_8$, alkylthio or a 5- to 10-membered heteroaryl ring. In certain examples, $R^3$ is an isobutyl group.

m can be 0, 1, or 2. When in is zero, the residue within the brackets is not present, and the boronate ester compound is a dipeptide. Similarly, when m is 1, the residue within the brackets is present, and the compound is a tripeptide. When m is 2, the compound is a tetrapeptide. In certain examples, in is zero. The terms "peptide," "dipeptide," and "tripeptide," as used here, are intended to encompass compounds comprising natural amino acid residues, unnatural amino acid residues, or a combination of natural and unnatural amino acid residues. It will be apparent that the terms "peptide," "dipeptide," and "tripeptide" are used to refer to compounds herein in which the carboxylic acid functionality of the C-terminal amino acid residue is replaced by a boronate ester functionality.

As used herein, the term "moiety derived from a polyol" refers to a moiety formed by removing the hydrogen atoms from two hydroxyl groups of a polyol (i.e., a moiety that includes two or more hydroxyl groups). The polyol can include any number of hydroxyl groups. For example, in some examples, the polyol can include from 2 to 8 hydroxyl groups (e.g., from 2 to 6 hydroxyl groups). In certain examples, the polyol can include at least 3 hydroxyl groups (e.g., from 3 to 8 hydroxyl groups, from 3 to 6 hydroxyl groups, or from 3 to 5 hydroxyl groups).

The moiety derived from a polyol can be attached to the boron atom by any two hydroxyl groups of the polyol, such that the resulting boronate ester forms 5-, 6-, 7-, 8-, or 9-membered ring. In some examples, the boronate ester forms a 5- or 6-membered ring. In certain examples, the polyol can include a 1,2-diol or 1,3-diol functionality.

The polyol can be any suitable polyol. For example the polyol can be a polymeric polyol (e.g., polyvinyl alcohol), an aromatic polyol (e.g., a catechol or catechol derivative), or a sugar (e.g., a monosaccharide, a disaccharide, an oligosaccharide, or a polysaccharide). In some embodiments, the polyol can be a non-aromatic polyol (i.e., the polyol does not include an aromatic moiety), In some examples, the polyol comprises a sugar (e.g., a monosaccharide such as fructose). In certain examples, the polyol can comprise a reduced sugar (e.g., a sugar alcohol such as mannitol, sorbitol, or galactitol). In certain examples, the polyol can comprise an amino sugar (e.g., meglumine or giucamine). In certain examples, the polyol is meglumine, glucamine, mannitol, sorbitol, or fructose.

In some examples, L is absent (i.e., Z is directly bound to A). As such contemplated herein are formula as disclosed herein where —Z-L-A is shown as Z-A. In other examples, L is present, and is a linking group. The linking group can be, for example, an alkylene, heteroalkylene, alkenylene, heteroalkenylene, alkynylene, heteroalkynylene, cycloalkylene, alkylcycloalkylene, cycloalkylalkylene, heterocyclylene, alkylheterocyclylene, heterocyclylalkylene, alkylcarbonyl, alkoxycarbonyl, alkylaminocarbonyl, heteroalkylaminocarbonyl, dialkylaminocarbonyl, or heterodialkylaminocarbonyl group through which Z is bound to A. Optionally, such linking groups can further include one or more functional groups, such as the linking moieties described below. The linking group can also be a linking moiety that links Z to A. Suitable linking moieties are known in the art, and include, for example, secondary amides (—CONH—), tertiary amides (—CONR—), secondary carbamates (—OCONH—; —NHCOO—), tertiary carbamates (—OCONR—; —NRCOO—), ureas (—NHCONH—; —NRCONH—; —NHCONR—, —NRCONR—), carbinols (—CHOH—, —CROH—), ethers (—O—), and esters (—COO—, —CH$_2$O$_2$C—), imines, and disulfide linkages, wherein R is an alkyl group, an aryl group, or a heterocyclyl group.

A can be any suitable lipophilic moiety. The lipophilic moiety can comprise a moiety derived from a lipid (e.g., a moiety formed by covalent reaction of a lipid with Z or L, when present). The lipid can be any suitable naturally occurring or synthetic lipid. For example, the lipid can comprise a fatty acid, a glycerolipid, a phospholipid, a sphingolipid, a sterol, or a prenol.

In some examples, the lipid can comprise a fatty acid. Fatty acids include a hydrocarbon chain that terminates with a carboxylic acid group. In some examples, the fatty acid can include at least 12 carbon atoms. The fatty acid can be a saturated, monounsaturated or polyunsaturated fatty acid. In some examples, the fatty acid can be a fatty acid that is naturally occurring in humans. Examples of suitable fatty acids that can be employed, either alone or as part of a larger lipid, include myristic (12:0, tetradecanoic), palmitic (16:0, hexadecanoic), stearic (18:0, octadecanoic), arachidic (20:0, eicosanoic), and behenic (22:0, docosanoic) saturated fatty acids; palmitoleic (16:1(n-7), cis-9-hexadecenoic), petroselinic (18:1(n-12), cis-6-octadecenoic), oleic (18:1(n-9), cis-octadecenoic, cis-vaccenic (18:1(n-7), cis-11-octadecenoic), erucic (22:1(n-9), cis-13-docosenoic monounsaturated fatty acids; and linoleic (18:2(n-6), 9,12-octadecadienoic), γ-linolenic (18:3(n-6), 6,9,12-octadecatrienoic), α-linolenic (18:3(n-3), 9,12,15-octatrienoic), arachidonic (20:4(n-6), 5,8,11,14,17-eicosatetraenoic), EPA (20:5(n-3), 5,8,11,14, 17-eicosapentaenoic), and DHA (22:6(n-3), 4,7,10,13,16, 19-docasahexaenoic)polyunsaturated acids.

Fatty acid derivatives with substituents or branching along the carbon chain can also be used in the present invention provided that the lipid character of the derivatized fatty acid is maintained. For example, the fatty acid can be a branched chain fatty acid possessing from 10 to 30 carbon atoms. Branches can include one or more methyl groups substituted at any position along the saturated or unsaturated fatty acid chain, or involve larger alkyl groups. Other useful fatty acids include those with one or more alicyclic rings along the fatty acid backbone or at a terminal position. Further useful fatty acids also include hydroxy fatty acids, wherein the hydroxy group is within two carbons of the carboxylic acid (α- and β-hydroxy fatty acids). The α- or β-hydroxy group of the hydroxy fatty acids can also be further derivatized through the formation of ethers or ester to add a second fatty acid chain to the lipid, thereby increasing its lipophilic character. The preceding discussion of fatty acids also applies to their use in the following types of lipids where the lipids contain fatty acid components.

In addition to being used in their naturally occurring form, the above fatty acids can be modified to better facilitate covalent or noncovalent binding to Z or L by, for example, converting the acid head group to an alcohol or amine, an alcohol further derivatized as a leaving group, or a leaving group. As well, the fatty acid can be derivatized by adding a short spacer, e.g., formation of esters with 2-aminoethanol, ethylene glycol or other ethanol derivatives possessing a desired functional group. All chemistry required to prepare such modified fatty acids are believed to be routine and known by chemists skilled in organic synthesis.

In some examples, the lipid can comprise a fatty amide. Fatty amides are amide analogues of fatty acids. Suitable fatty amides include those in which a fatty acid, as described above, is converted to an amide by, for example, treatment with 2-aminoethanol, thus providing an alcohol that can be further modified, if desired. Similarly, fatty amides can be formed using diamines, such as 1,2-diaminoethane, thus providing a primary amine for facilitating linkage to Z or L. Suitable fatty amides can also be formed using fatty acids and amino acids, which can then be further derivatized, if desired. Example fatty amides include anandamide, N-arachidonoylglycine, and N-palmitoylethanolamide.

In some examples, the lipid can comprise a glycerolipid. Suitable glycerolipids include mono- and diacylglycerolipids (e.g., mono- and diacylglycerols and glycosylglycerols) that include fatty acids, as described above.

In some examples, the lipid can comprise a phospholipid. Examples of suitable phospholipids include phosphatidylethanolamines (cephalins), phosphatidylcholines, phosphatidylserines, phosphatidyl-L-threonines, phosphatidylglycerols, phosphatidylinositols, phosphatidic acids, bisphosphatidyl glycerols (cardiolipins), and phosphoglycolipids. Other suitable phospholipids include ether phospholipids (e.g., alkylacyl phospholipids and alkenylacyl phospholipids), lysophospholipids, and any of the above phospholipids in which one of the fatty acid chains has been hydrolyzed to give a monoacyl, monoalkyl or monoalkenyl-phospholipid.

In some examples, the lipid can comprise a sphingolipid. Examples of suitable sphingolipids include sphingosine and other sphingoid bases, ceramides, ceramide phospholipids, and glycosphingolipids. Examples of ceramide phospholipids include sphingolipids other than sphingomyelin in which a ceramide is bound to a phosphate group (e.g., sphingolipids such as ceramide phosphorylethanolamines, ceramide phosphorylglycerols, and ceramide inositols). Suitable sphingoid bases can include analogues of sphingoid bases with differing carbon chains (length, unsaturation, hydroxylation). In some examples, the carbon chains in the sphingoid base can include from 14-24 carbon atoms. Suitable sphingoid bases include sphingosine d18:1, d18:1$^{\Delta 4t}$, 4E-d18:1, or its cis isomer: d18:1$^{\Delta 4c}$, 4Z-d18:1) dihydrosphingosine (d18:0, sphinganine), phytosphingosine (t18:0), and dehydrophytosphingosine (t18:1, t18:1$^{\Delta 8t}$, 8E-t18:1, or is cis isomer: t18:1$^{\Delta 8c}$, 8Z-t18:1), and eicosasphingosine (d20:1, 4E-d20:1, d20:1$^{\Delta 4t}$).

In some examples, the lipid can comprise a sterol. Suitable sterol lipids include sterols, and oxysterols in which the A or B ring of the cholesterol is oxidized rather than the alkyl chain, such as 7β-hydroxycholesterol or 4β-hydroxycholesterol. Other suitable oxysterols include oxysterols in which the alkyl side chain of the cholesterol has been hydroxylated (and optionally converted to an amine) and the A and B rings of the cholesterol skeleton are in a reduced form (i.e., dehydroxylated). Other suitable oxysterols include oxysterols possessing a primary hydroxy group that is oxidized to a carboxylic acid, including examples where the carboxylic acid has been esterified (e.g., with 2-aminoethanol).

In addition to the sterols commonly found in mammals, suitable sterols can include sterols from other origins, such as plant-based sterols (phytosterols). Example phytosterols include, but are not limited to, campesterol, sitosterol, brassicasterol, stigmasterol, avenasterol.

Other suitable sterols include derivatized sterols. Sterols can also be derivatized by adding, for example, 2-aminoethanol, inositol, serine, glycoside, phosphorylethanolamine, phosphonylethanolamine, phosphorylserine, phosphorylinositol, phosphorylglycosides, or glycosides derivatized with 2-aminoethanol, serine, phosphorylethanolamine, or phosphonylethanolamine, to the 3-hydroxy substituent of the A-ring or a hydroxy substituent of the alkyl side chain of any of the above sterols or oxysterols.

In some examples, the lipid can comprise a prenol. Suitable prenol lipids can include fat-soluble vitamins (e.g., vitamins A, E, and K), as well as other prenol lipids, including other tocopherols, tocotrienols, retinoic acid, dolichols, and polyprenols. Other suitable prenols include diphosphate derivatives of prenols, such as farnesyl pyrophosphate and presqualene diphosphate. Prenol lipids can also be further derivatized by, for example, adding 2-aminoethanol, inositol, serine, glycoside, phosphorylethanolamine, phosphonylethanolamine, phosphorylserine, phosphorylinositol, phosphorylglycosides, or glycosides derivatized with 2-aminoethanol, serine, phosphorylethanolamine, or phosphonylethanolamine, to an available hydroxy substituent.

In some examples, A is a $C_8$-$C_{40}$ alkyl group, a $C_8$-$C_{40}$ alkenyl group, a $C_8$-$C_{40}$ alkoxy group, a $C_8$-$C_{40}$ alkylthio group, a $C_8$-$C_{40}$ alkylsulfinyl group, a $C_8$-$C_{40}$ alkylsulfonyl group, a $C_8$-$C_{40}$ alkylamino group, a $C_8$-$C_{40}$ dialkylamino group, a $C_8$-$C_{40}$ alkylcarbonyl group, a $C_8$-$C_{40}$ alkoxycarbonyl group, a $C_8$-$C_{40}$ alkylaminocarbonyl group, a $C_8$-$C_{40}$ dialkylaminocarbonyl group, or a moiety defined by the formula below

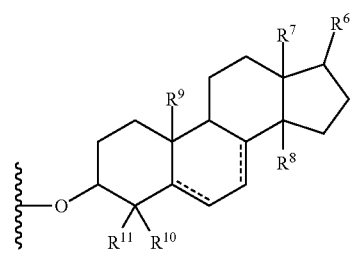

wherein the dotted lines indicate that a single or double bond can be present;

$R^6$ is an alkyl group, an alkenyl group, an alkynyl group, an aryl group, an alkylaryl group, an arylalkyl group, a cycloalkyl group, an alkylcycloalkyl group, a heterocyclyl group, an alkylheterocyclyl group, a heteroaryl group, an alkytheteroaryl group, an alkoxy group, or an alkylthio group; and $R^7$, $R^8$, $R^9$, $R^{10}$, and $R^{11}$ are independently hydrogen, a hydroxy group, an amino group, an alkyl group, an alkenyl group, an alkynyl group, an aryl group, an alkylaryl group, arylalkyl group, a cycloalkyl group, an alkylcycloalkyl group, a heterocyclyl group, an alkylheterocyclyl group, a heteroaryl group, an alkylheteroaryl group, an alkoxy group, an alkylthio group, an alkylsulfinyl group, an alkylsulfonyl group, an alkylamino group, a dialkylamino group, an alkylcarbonyl group, an alkoxycarbonyl group, an alkylaminocarbonyl group, or a dialkylaminocarbonyl group.

In certain examples, A is a moiety defined by the formula below

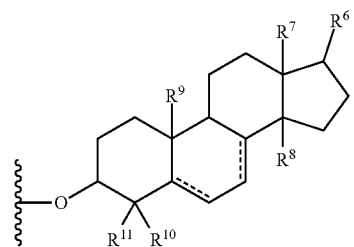

where the dotted lines indicate that a single or double bond can be present; and $R^6$, $R^7$, $R^8$, $R^9$, $R^{10}$, and $R^{11}$ are as defined above. In one embodiment, A is defined by the structure below.

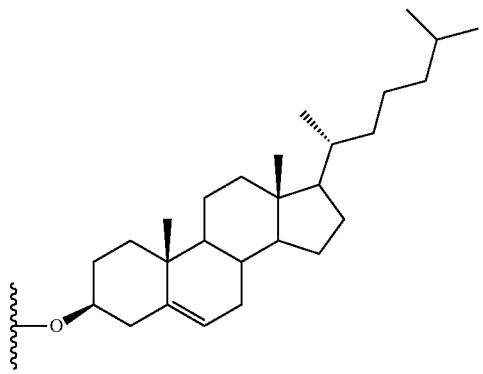 [SMILES: *O[C@H]1CC[C@@]2(C)C(=CCC3C4CCC([C@H](C)CCCC(C)C)[C@@]4(C)CCC32)C1]

In certain examples, the compound can be defined by Formula IA

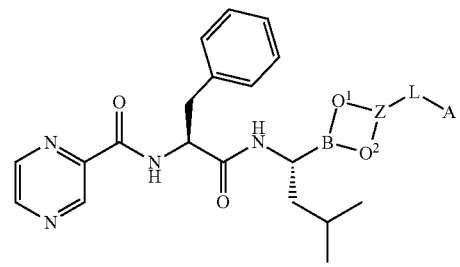

Formula IA where Z, L, and A are as defined above with respect to Formula I.

In certain examples, the compound can be defined by Formula II

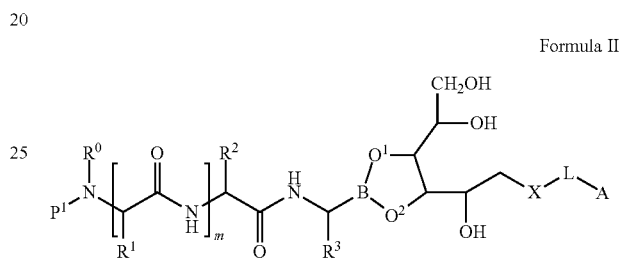

Formula II wherein $P^1$, $R^0$, $R^1$, $R^2$, $R^3$, $R^4$, m, L, and A are as defined above with respect to Formula I, X is —O— or $NR^{12}$—; and $R^{12}$ is hydrogen or an alkyl group.

In certain examples, $R^{12}$ is hydrogen. In other examples, $R^{12}$ is an alkyl group. For example, in some examples, $R^{12}$ can be a $C_1$-$C_6$ alkyl group. In some examples, $R^{12}$ can be $C_1$-$C_4$ alkyl group. In certain examples, $R^{12}$ can be methyl or ethyl.

In certain examples, X is —O—. In other examples, X is —NH— or —N(CH$_3$)—.

In certain examples, the compound can be defined by Formula IIA

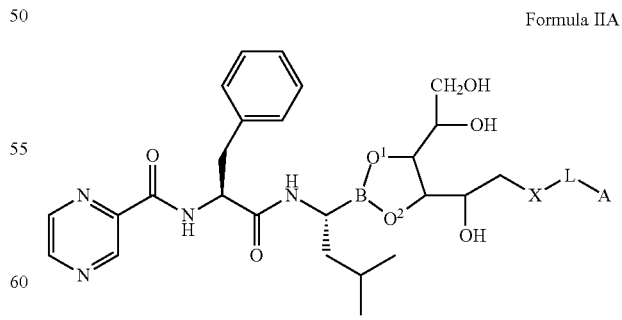

Formula IIA wherein X, $R^{12}$, L, and A are as defined above with respect to Formula II.

In certain examples, the compound can be one of the following.

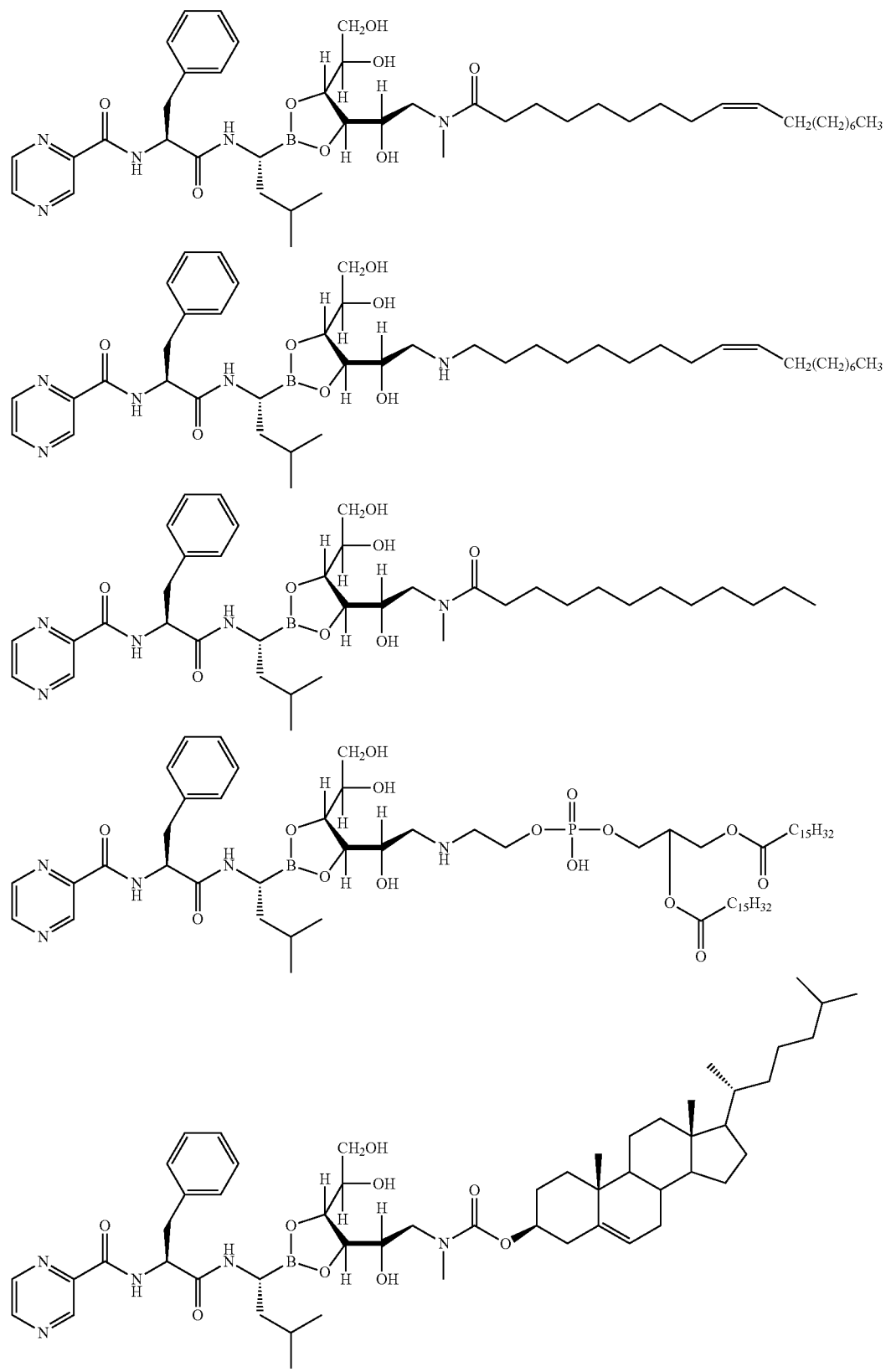
Pharmaceutical Formulations
Also provided are pharmaceutical formulations including the compounds described herein. Pharmaceutical formulations can include a therapeutically effective amount of a compound described herein in combination with one or more pharmaceutically acceptable excipients. Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials that are generally recognized as safe (GRAS) by the FDA, and can be administered to an individual without causing undesirable biological side effects or unwanted interactions.

In certain examples, the pharmaceutical formulation can be a liposomal formulation. For example, provided herein are pharmaceutical formulations that include liposomes formed from a vesicle-forming lipid, and a compound described herein entrapped in the liposomes. A compound entrapped in a liposome can be sequestered in the central aqueous compartment of the liposome, in the aqueous space between liposome lipid bilayers, or within a bilayer of the liposome The liposomes in the formulation can be composed primarily of vesicle-forming lipids. Such a vesicle-forming lipid is one that can form spontaneously into bilayer vesicles in water, as exemplified by the phospholipids, with its hydrophobic moiety in contact with the interior, hydrophobic region of the bilayer membrane, and its head group moiety oriented toward the exterior, polar surface of the membrane. Lipids capable of stable incorporation into lipid bilayers, such as cholesterol and its various analogs, can also be used in the liposomes. The vesicle-forming lipids are preferably lipids having two hydrocarbon chains, typically acyl chains, and a head group, either polar or nonpolar. There are a variety of synthetic vesicle-forming lipids and naturally-occurring vesicle-forming lipids, including the phospholipids, such as phosphatidylcholine, phosphatidylethanolamine, phosphatidic acid, phosphatidylinositol, and sphingomyelin, where the two hydrocarbon chains are typically between about 14-22 carbon atoms in length, and have varying degrees of unsaturation. The above-described lipids and phospholipids whose acyl chains have varying degrees of saturation can be obtained commercially or prepared according to published methods. Other suitable lipids include glycolipids, cerebrosides and sterols, such as cholesterol.

The vesicle-forming lipid can be selected to achieve a specified degree of fluidity or rigidity, to control the stability of the liposome in serum, and/or to control the rate of release of the entrapped agent in the liposome. Liposomes having a more rigid lipid bilayer, or a gel-phase bilayer, are achieved by incorporation of a relatively rigid lipid, e.g., a lipid having a relatively high phase transition temperature, e.g., up to 60° C. Rigid, i.e., saturated, lipids contribute to greater membrane rigidity in the lipid bilayer. Other lipid components, such as cholesterol, are also known to contribute to membrane rigidity in lipid bilayer structures. On the other hand, lipid fluidity is achieved by incorporation of a relatively fluid lipid, typically one having a lipid phase with a relatively low gel to liquid-crystalline phase transition temperature, e.g., at or below room temperature.

The liposomes can optionally include a vesicle-forming lipid covalently linked to a hydrophilic polymer. As has been described, for example in U.S. Pat. No. 5,013,556, including such a polymer-derivatized lipid in the liposome composition forms a surface coating of hydrophilic polymer chains around the liposome. The surface coating of hydrophilic polymer chains is effective to increase the in vivo blood circulation lifetime of the liposomes when compared to liposomes lacking such a coating. Polymer-derivatized lipids comprised of methoxy(polyethylene glycol) (mPEG) and a phosphatidylethanolamine (e.g., dimyristoyl phosphatidylethanolamine, dipalmitoyl phosphatidylethanolamine, distearoyl phosphatidylethanolamine (DSPE), or dioleoyl phosphatidylethanolamine) can be obtained from Avanti Polar Lipids, Inc. (Alabaster, Ala.) at various mPEG molecular weights (350, 550, 750, 1,000, 2,000, 3,000, and 5,000 Daltons). Lipopolymers of mPEG-ceramide can also be purchased from Avanti Polar Lipids, Inc. Preparation of lipid-polymer conjugates is also described in the literature, see U.S. Pat. Nos. 5,631,018, 6,586,001, and 5,013,556; Zalipsky, S. et. al., *Bioconjugate Chem.* 8:111 (1997); Zalipsky, S. et al., *Meth. Enzymol.* 387:50 (2004). These lipopolymers can be prepared as well-defined, homogeneous materials of high purity, with minimal molecular weight dispersity (Zalipsky, S. et al., *Bioconjugate Chem.* 8:111 (1997); Wong, J. et al., *Science* 275:820 (1997)). The lipopolymer can also be a "neutral" lipopolymer, such as a polymer-distearoyl conjugate, as described in U.S. Pat. No. 6,586,001, incorporated by reference herein.

When a lipid-polymer conjugate is included in the liposomes, typically between 1-20 mole percent of the lipid-polymer conjugate is incorporated into the total lipid mixture (see, e.g., U.S. Pat. No. 5,013,556).

If desired for a particular application, the liposomes can include a ligand, such as a targeting ligand, conjugated to the liposome. For example, the liposomes can optionally include a lipopolymer modified to include a ligand, forming a lipid-polymer-ligand conjugate, also referred to herein as a 'lipopolymer-ligand conjugate'. The ligand can be a therapeutic molecule, such as a drug or a biological molecule having activity in vivo, a diagnostic molecule, such as a contrast agent or a biological molecule, or a targeting molecule having binding affinity for a binding partner, preferably a binding partner on the surface of a cell. For example, the ligand can have binding affinity for the surface of a cell, so as to facilitate entry of the liposome into the cytoplasm of a cell via internalization. A ligand present in liposomes that include such a lipopolymer-ligand is oriented outwardly from the liposome surface, and therefore available for interaction with its cognate receptor.

Methods for attaching ligands to lipopolymers are known, where the polymer can be functionalized for subsequent reaction with a selected ligand. (U.S. Pat. No. 6,180,134; Zalipsky, S. et al., *FEBS Lett.* 353:71 (1994); Zalipsky, S. et al., *Bioconjugate Chem.* 4:296 (1993); Zalipsky, S. et al., *J. Control. Rel.* 39:153 (1996); Zalipsky, S. et al., *Bioconjugate Chem.* 8(2):111 (1997); Zalipsky, S. et al., *Meth. Enzymol.* 387:50 (2004)). Functionalized polymer-lipid conjugates can also be obtained commercially, such as end-functionalized PEG-lipid conjugates (Avanti Polar Lipids, Inc.). The linkage between the ligand and the polymer can be a stable covalent linkage or a releasable linkage that is cleaved in response to a stimulus, such as a change in pH or presence of a reducing agent.

The ligand can be a molecule that has binding affinity for a cell receptor or for a pathogen circulating in the blood. The ligand can also be a therapeutic or diagnostic molecule, in particular molecules that when administered in free form have a short blood circulation lifetime. In one embodiment, the ligand is a biological ligand, such as a ligand having binding affinity for a cell receptor. Example biological ligands include molecules having binding affinity to receptors for CD4, folate, insulin, LDL, vitamins, transferrin, asialoglycoprotein, selectins, such as E, L, and P selectins, Flk-1,2, FGF, EGF, integrins, in particular, $\alpha_4\beta_1$ $\alpha_v\beta_3$, $\alpha_v\beta_1$ $\alpha_v\beta_5$, $\alpha_v\beta_6$ integrins, HER2, and others. Ligands are known in the art, and can include proteins and peptides, including antibodies and antibody fragments, such as F(ab')$_2$, F(ab)$_2$, Fab', Fab, Fv (fragments consisting of the variable regions of the heavy and light chains), and scFv (recombinant single chain polypeptide molecules in which light and heavy variable regions are connected by a peptide linker), and the like. The ligand can also be a small molecule peptidomimetic. It will be appreciated that a cell surface receptor, or fragment thereof, can serve as the ligand. Other example targeting ligands include, but are not limited to vitamin molecules (e.g., biotin, folate, cyanocobalamine), oligopeptides, oligosaccharides. Other example ligands include those described in U.S. Pat. Nos. 6,214,388, 6,316,024, 6,056,973, and 6,043,094, which are herein incorporated by reference.

Liposomal formulations including the compounds described herein can be formed using any suitable method for preparing and/or loading liposomes. For example, a compound described herein and one or more vesicle-forming lipids can be dissolved in a suitable solvent, and the solvent can be evaporated to form a lipid film. The lipid film can be hydrated with an aqueous solution (e.g., having a pH of from 7-9) to form liposomes comprising the entrapped compound.

After liposome formation, the liposomes can be sized to obtain a population of liposomes having a substantially homogeneous size range, for example from 0.01 to 0.5 microns e.g., from 0.03-0.40 microns). Liposomes can be sized by any suitable method, such as by extrusion through a series of membranes having a selected uniform pore size (e.g., polycarbonate membranes having a selected uniform pore size in the range of 0.03 to 0.2 micron). The pore size of the membrane corresponds roughly to the largest sizes of liposomes produced by extrusion through that membrane, particularly where the preparation is extruded two or more times through the same membrane. Homogenization methods can also be used to prepare liposomes having sizes of 100 nm or less (Martin, F. J., in *Specialized Drug Delivery Systems—Manufacturing and Production Technology*, P. Tyle, Ed., Marcel Dekker, New York, pp. 267-316 (1990)).

In some embodiments, the liposomes in the formulation can have an average particle size, as measured by dynamic light scattering, of from 50 nm to 250 nm (e.g., from 50 nm to 200 nm, from 75 nm to 150 nm, from 90 nm to 150 nm, from 12.0 nm to 150 nm, from 100 nm to 130 nm, or from 90 nm to 110 nm). In some embodiments, the liposomes in the formulation can have a zeta potential of from −50 mV to 0 mV (e.g., from −25 mV to 0 mV, from −15 mV to 0 mV, or from −10 mV to 0 mV).

After sizing, unencapsulated compound can be removed by a suitable technique, such as dialysis, centrifugation, tangential-flow diafiltration, size exclusion chromatography, or ion exchange to achieve a suspension of liposomes having a high concentration of entrapped compound in the liposomes and little to no compound in solution outside of the liposomes. Also after liposome formation, the external phase of the liposomes can be adjusted, if desired, by titration, dialysis or the like, to an appropriate pH.

Once formed, the liposomal suspension can be lyophilized using methods known in the art. The resulting composition can be in the form of a lyophilized powder. The term "lyophilized powder" refers to any solid material obtained by lyophilization of an aqueous mixture. In some examples, a lyoprotectant, such as sucrose or trehalose, can be added to the liposomal formulation prior lyophilization.

Stability of the lyophilized formulation can be assessed by visual inspection for appearance of cake, the time of reconstitution, and the property of the reconstituted liposomes after various lengths of storage time. In terms of quantitative standard, a liposomal formulation can be assessed for appearance of particulates or turbidity by visual inspection, change in color, mean particle size and polydispersity index by dynamic light scattering on a particle size analyzer (e.g., using a NICOMP370 particle sizing system), zeta potential measurement (e.g., using Malvern Instrument's Zetasizer), percentage of drug encapsulation by chromatography (e.g., by size-exclusion chromatography on a Sepharose CL-4B column), chemical integrity of the drug substance and of excipients and appearance of decomposition products by HPLC and by LC-MS. The preferred stability range for the BTZ liposome formulation is less than 20% change in mean particle size and drug encapsulation percentage after 6 months storage at 4 degree compared to immediately reconstituted sample; less than 5% chemical decomposition of the drug product.

Lyophilized formulations can be readily reconstituted prior to administration by adding an aqueous solvent. The reconstitution solvent can be suitable for pharmaceutical administration (e.g., for parenteral administration to a subject) Examples of suitable reconstitution solvents include, without limitation, water, saline, and phosphate buffered saline (PBS).

The liposomal formulation described herein can be used in combination with other anticancer agents, including various chemotherapeutic agents, such as cytarabine, fludarabine, decitabine, daunorubicin, and therapeutic antibodies such as rituximab, alemtuzumab, tyrosine kinase inhibitors, and any other agents with anticancer activities. In addition, anticancer agents can be co-formulated in the same liposome formulation as the boronic acid agent. For example, daunorubicin or cytarabine can be co-encapsulated into liposomal bortezomib at a defined drug ratio. Such type of combination can mediate co-delivery of the therapeutic combination at a ratio that produces optimal therapeutic synergism.

Methods of Use

Also provided herein are methods of treating cancer. Methods of treating cancer can include administering to a subject a therapeutically effective amount of a compound or formulation described herein. The compounds described herein can function as proteasome inhibitors. Proteasome inhibitors induce apoptosis of cells by their ability to inhibit cellular proteasome activity. More specifically, in eukaryotic cells, the ubiquitin-proteasome pathway is the central pathway for protein degradation of intracellular proteins. Proteins are initially targeted for proteolysis by the attachment of a polyubiquitin chain, and then rapidly degraded to small peptides by the proteasome and the ubiquitin is released and recycled. This coordinated proteolytic pathway is dependent upon the synergistic activity of the ubiquitin-conjugating system and the 26S proteasome. The 26S proteasome is a large (1,500-2,000 kDa) multi-subunit complex present in the nucleus and cytoplasm of eukaryotes. The catalytic core of this complex, referred to as the 20S proteasome, is a cylindrical structure consisting of four heptameric rings containing $\alpha$- and $\beta$-subunits. The proteasome is a threonine protease, the N-terminal threonine of the $\beta$-subunit providing the nucleophile that attacks the carbonyl group of the peptide bond in target proteins. At least three distinct proteolytic activities are associated with the proteasome: chymotryptic, tryptic and peptidylglutamyl. The ability to recognize and bind polyubiquitinated substrates is conferred by 19S (PA700) subunits, which bind to each end of the 20S proteasome. These accessory subunits unfold substrates and feed them into the 20S catalytic complex, whilst removing the attached ubiquitin molecules. Both the assembly of the 26S proteasome and the degradation of protein substrates are ATP-dependent (Almond, *Leukemia* 16:433 (2002)).

The ubiquitin-proteasome system regulates many cellular processes by the coordinated and temporal degradation of proteins. By controlling levels of many key cellular proteins, the proteasome acts as a regulator of cell growth and apoptosis and disruption of its activity has profound effects on the cell cycle. For example, defective apoptosis s involved in the pathogenesis of several diseases including certain cancers, such as B cell chronic lymphocytic leukemia, where there is an accumulation of quiescent tumor cells.

Proteasome inhibitors as a class of compounds in general act by inhibiting protein degradation by the proteasome. The class includes peptide aldehydes, peptide vinyl, sulfones, which act by binding to and directly inhibiting active sites within the 20S core of the proteasome. Peptide aldehydes and peptide vinyl sulfones, however, bind to the 20S core particle in an irreversible manner, such that proteolytic activity cannot be restored upon their removal. In contrast, peptide boronic acid compounds, such as those described herein, confer stable inhibition of the proteasome, yet dissociate slowly from the proteasome. The peptide boronic acid compounds are more potent than their peptide aldehyde analogs, and act more specifically in that the weak interaction between boron and sulfur means that peptide boronates do not inhibit thiol proteases (Richardson, P. G., et al., *Cancer Control*. 10(5):361, (2003)).

Exposure of a variety of tumor-derived cell lines to proteasome inhibitors triggers apoptosis, likely as a result of effects on several pathways, including cell cycle regulatory proteins, p53, and nuclear factor kappa B (NF-κB) (Grimm, L. M. and Osborne, B. A., *Results Probl. Cell. Differ.* 23:209-28 (1999); Orlowski, R. Z., *Cell Death Differ*. 6(4): 303-13 (1999)). Many of the initial studies documenting proteasome inhibitor-mediated apoptosis used cells of hematopoietic origin, including monoblasts (Imajoh-Ohmi, S. et al., *Biochem. Biophys. Res. Commun.* 217(3):1070-77 (1995)), T-cell and lymphocytic leukemia cells (Shinohara, K. et al., *Biochem. J.* 317(Pt 2):385-88, (1996)), lymphoma cells (Tanimoto, Y. et al., *J. Biochem.* (Tokyo) 121 (3):542-49 (1997)), and promyelocytic leukemia cells (Drexler, H. C., *Proc. Natl. Acad. Sci. U.S.A.* 94(3):855-60 (1997)). The first demonstration of in vivo antitumor activity of a proteasome inhibitor used a human lymphoma xenograft model (Orlowski, R. Z. et al., *Cancer Res* 58(19):4342-48 (1998)). Furthermore, proteasome inhibitors were reported to induce preferential apoptosis of patient-derived lymphoma (Orlowski, R. et al. *Cancer. Res.*, 58:(19):4342 (1998)) and leukemia cells (Masdehors, P. et al., *Br. J. Haematol.* 105 (3):752-57 (1999)) and to preferentially inhibit proliferation of multiple myeloma cells (Hideshima, T. et al., *Cancer Res.*, 61(7): 3071-76 (2001)) with relative sparing of control, non-transformed cells. Thus, proteasome inhibitors are particularly useful as therapeutic agents in patients with refractory hematologic malignancies.

In one embodiment, a compound or formulation described herein is used for treatment of cancer, and more particularly for treatment of a tumor in a cancer patient. The cancer can be a tumor. The cancer can also be stomach cancer, kidney cancer, bone cancer, liver cancer, brain cancer, skin cancer, oral cancer, lung cancer, pancreatic cancer, colon cancer, intestinal cancer, myeloid leukemia, melanoma, glioma, thyroid follicular cancer, bladder carcinoma, myelodysplastic syndrome, breast cancer, low grade astrocytoma, astrocytoma, glioblastoma, medulloblastoma, renal cancer, prostate cancer, endometrial cancer, or a neuroblastoma.

In certain examples, the cancer can be multiple myeloma. Multiple myeloma is an incurable malignancy that is diagnosed in approximately 15,000 people in the United States each year (Richardson, R G. et al., *Cancer Control*. 10(5): 361 (2003)). It is a hematologic malignancy typically characterized by the accumulation of clonal plasma cells at multiple sites in the bone marrow. The majority of patients respond to initial treatment with chemotherapy and radiation; however, most eventually relapse due to the proliferation of resistant tumor cells. In one embodiment, provided are methods for treating multiple myeloma in a subject that can comprise administering a liposome formulation comprising a compound described herein.

In certain examples, the cancer cancer breast cancer. The compounds and formulations described herein can be effective in breast cancer treatment by helping to overcome some of the major pathways by which cancer cells resist the action of chemotherapy. For example, signaling through NF-κB, a regulator of apoptosis, and the p44/42 mitogen-activated protein kinase pathway, can be anti-apoptotic. Since proteasome inhibitors block these pathways, the compounds are able to activate apoptosis. Thus, in one embodiment, provided are methods for treating breast cancer in a subject that can comprise administering a liposome formulation comprising a compound described herein. Moreover, since chemotherapeutic agents such as taxanes and anthracyclines have been shown to activate one or both of these pathways, use of a proteasome inhibitor in combination with conventional chemotherapeutic agents acts to enhance the antitumor activity of drugs, such paclitaxel and doxorubicin. Thus, in another embodiment, provided are methods of treating cancer in which a chemotherapeutic agent, in free form or in liposome-entrapped form, is administered in combination with a compound or formulation described herein.

Doses and a dosing regimen for the compounds and formulations described herein will depend on the cancer being treated, the stage of the cancer, the size and health of the patient, and other factors readily apparent to an attending medical caregiver. Clinical studies with the proteosome inhibitor bortezomib, Pyz-Phe-boroLeu (PS-341), can be used to provide guidance for selecting suitable dosages and dosing regimens. For example, given intravenously once or twice weekly, the maximum tolerated dose in patients with solid tumors was 1.3 mg/m² (Orlowski, R. Z. et al., *Breast Cancer Res*. 5:1-7 (2003)). In another study, bortezomib given as an intravenous bolus on days 1, 4, 8, and 11 of a 3-week cycle suggested a maximum tolerated dose of 1.56 mg/m² (Vorhees, P. M. et al., *Clinical Cancer Res*. 9:6316 (2003)). However, since liposomal BTZ is less toxic than free BTZ, the optimal clinical dose of the liposomal drug can be several times higher.

Administration

The compounds and formulations described herein can be administered parenterally (e.g., by intravenous administration or subcutaneous administration). It will be appreciated that the formulation can include any necessary or desirable pharmaceutical excipients to facilitate delivery. The compounds and formulation disclosed herein can also be administered via oral route, by i.p, injection, by intramuscular injection, intratumoral injection, and by airway administration as a micronized solid or liquid aerosol.

The term "administration" and variants thereof (e.g., "administering" a compound) in reference to a compound as described herein means introducing the compound or a formulation thereof into the system of a subject in need of treatment. When a compound as described herein or a formulation thereof is provided in combination with one or more other active agents (e.g., a cytotoxic agent, etc.), "administration" and its variants are each understood to include concurrent and sequential introduction of the compound or formulation thereof and other agents.

In vivo application of the disclosed compounds, and formulations containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or formulations can be a single administration, or at continuous or distinct intervals as can be readily determined by a person skilled in the art.

The compounds disclosed herein, and formulations comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's *Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The formulations used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The formulations also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total formulation including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. it should be understood that in addition to the ingredients particularly mentioned above, the compositions disclosed herein can include other agents conventional in the art having regard to the type of formulation in question.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy*, 1999, 10(18):17).

Therapeutic application of compounds and/or formulations containing them can be accomplished by any suitable therapeutic method and technique presently or prospectively known to those Skilled in the art. Further, compounds and compositions disclosed herein have use as starting materials or intermediates for the preparation of other useful compounds and compositions.

Compounds and formulations disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and formulations disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and formulations disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, tier example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer theta topically to the skin as formulations, in combination with a dermatologically acceptable carrier, which can be a solid or a liquid.

Compounds and agents and formulations disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. No. 4,608,392; U.S. Pat. No. 4,992,478; U.S. Pat. No. 4,559,157; and U.S. Pat. No. 4,820,508.

Useful dosages of the compounds and agents and pharmaceutical formulations disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation; East Hanover, N.J.) and HERCEPTIN (Genentech, Inc.; South San Francisco, Calif.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{113}$, $I^{125}$, $Y^{90}$, $P^{32}$, etc.), and toxins of bacterial, fungal, plant, or animal origin e.g., ricin, botulinum toxin, anthrax toxin, aflatoxin, jellyfish venoms (e.g., box jellyfish, etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

The disclosed subject matter also concerns a packaged dosage formulation comprising in one or more containers at least one inhibitor compound or composition disclosed herein, e.g., any compound of Formula I. A packaged dosage formulation can optionally comprise in one or more containers a pharmaceutically acceptable carrier or diluent.

Depending upon the disorder or disease condition to be treated, a suitable dose(s) can be that amount that will reduce proliferation or growth of the target cell(s). In the context of cancer, a suitable dose(s) is that which will result in a concentration of the act agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; oral, 0.01 to about 100 mg/kg; of animal (body) weight. In some embodiments, the dosage levels of the administered active ingredients can be: intravenous, 0.01 to about 25 mg/kg; intraperitoneal, 0.01 to about 5 mg/kg; subcutaneous, 0.01 to about 5 mg/kg; intramuscular, 0.01 to about 5 mg/kg; oral, 0.01 to about 5 mg/kg; of animal (body) weight. In some embodiments, the dosage levels of the administered active ingredients can be: intravenous, 0.01 to about 1 mg/kg; intraperitoneal, 0.01 to about 5 mg/kg; subcutaneous, 0.01 to about 5 mg/kg; intramuscular, 0.01 to about 5 mg/kg; oral, 0.01 to about 5 mg/kg; of animal (body) weight. In certain embodiments, the dosage levels of the administered active ingredients can be: intravenous, 0.01 to about 0.5 mg/kg; intraperitoneal, 0.01 to about 1 mg/kg; subcutaneous, 0.01 to about 1 mg/kg; intramuscular, 0.01 to about 1 mg/kg; oral, 0.01 to about 1 mg/kg; of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

By way of non-limiting illustration, examples of certain examples of the present disclosure are given below.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1. Preparation, Formulation, and Evaluation of BTZ-OMG

Synthesis of a Lipophilic Ester of BTZ-Oleoylmeglumine (BTZ-OMG)

Meglumine was reacted with oleoyl chloride at a 1:1 molar ratio to yield N-methyl-N((4R,5R)-2,3,4,5,6-pentahydroxyhexyl) oleamide (OMG) (Scheme 1). OMG was then coupled to BTZ to yield BTZ-OMG (Scheme 1).

Preparation of a Liposomal Formulation of BTZ-OMG

L-α-phosphatidylcholine (egg PC), cholesterol, 1,2-distearoyl-sn-glycero-3-phosphoethanolamine (DSPE) conjugated polyethylene glycol (PEG) (mPEG-DSPE), and BTZ-OMG were dissolved in chloroform at a molar ratio of 4038:2:20. Rotary evaporation was applied to form a dry lipid film, followed by hydration with calcium acetate buffer at a pH of 8. Extrusion was used to reduce the liposome size to 150 nm or less. Any remaining unencapsulated drug was then removed through size exclusion chromatography on a Sepharose CL-4B column. Finally, the liposomes were sterile filtered and lyophilized.

In some examples, the liposomes were made at pH 8, lyophilized in the presence of 10% sucrose as a lyoprotectant, and reconstituted shortly prior to use.

Particle Sizer Model 370. The encapsulation efficiency was examined by a UV-visible spectrophotometer as the OD at 270 nm after 1:9 methanol extraction of fractions from the Sepharose CL-4B column (FIG. 1). A reference measurement was also taken of the OD at 450 nm without methanol extraction (FIG. 1). Then, the ratio of total amount of drug content in the liposome fractions to total drug fractions was calculated. In this example, a drug entrapment of 41% was obtained.

In addition, one batch of this liposome without the removal of free drug was lyophilized. The loading efficiency was taken after rehydration, and the loading result appeared to be the same with or without lyophilization. This suggested that the liposomal formulation of BTZ-OMG maintained stability during lyophilization.

Scheme 1. Structure and synthesis of BTZ-OMG.

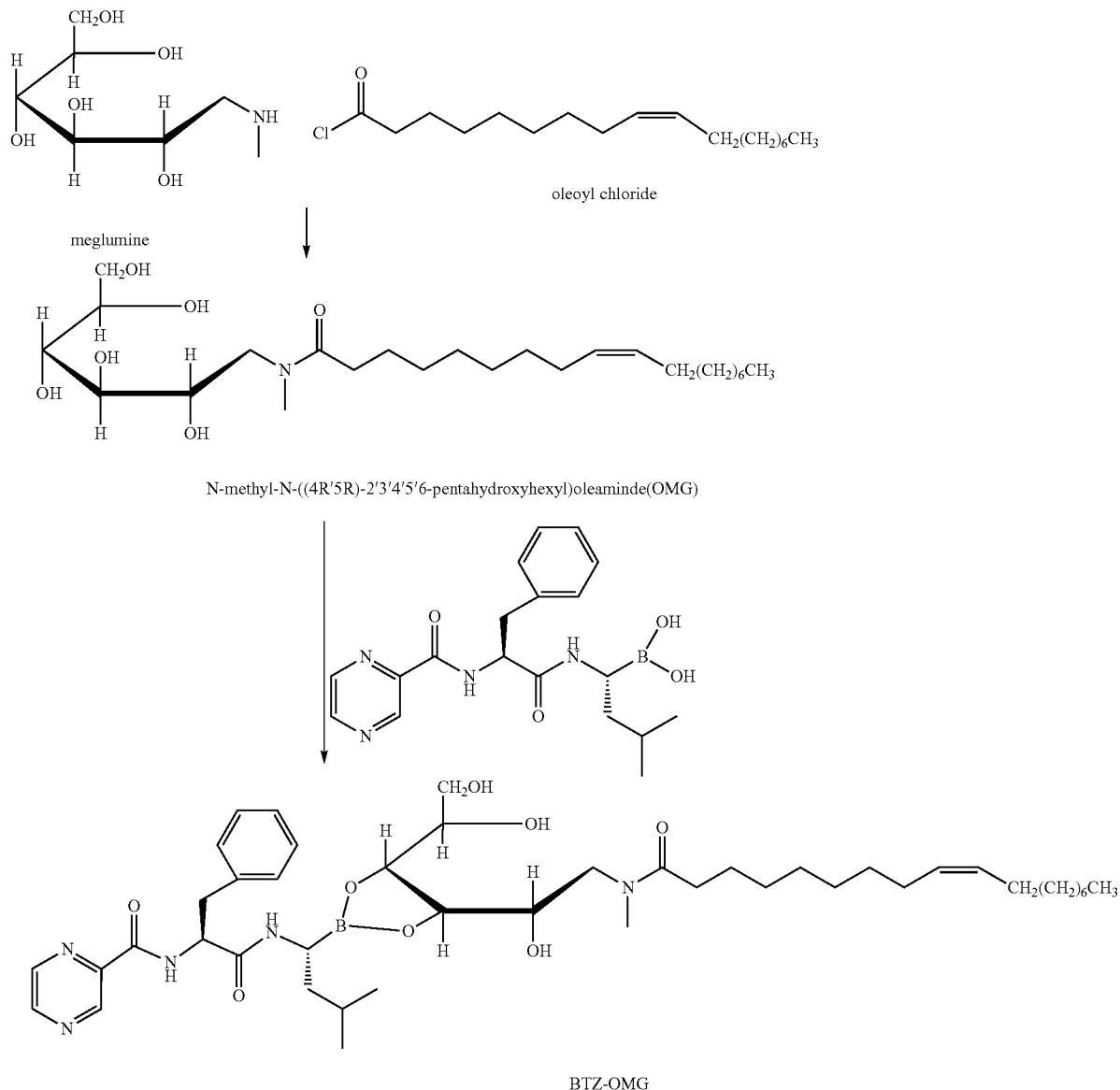

Characterization of the Liposomal Formulation of BTZ-OMG

The liposome particle size distribution is determined through dynamic light scattering on a NICOMP Submicron Example 2. Preparation of BTZ-OGA The synthetic methodology used to prepare BTZ-OGA is described in Scheme 2. Briefly, oleylglucamine (OGA) was synthesized from glucose, oleylamine and sodium cyanoborohydride using a Borch-type reductive amination. Then the OGA was coupled to BTZ, affording BTZ-OGA. (Scheme 2). D-glucose and oleylamine at 1:1 molar ratio were co-dissolved and stirred in tert-butanol for 24 hr. Next, the mixture was cooled to 0° C. in an ice bath and equal molar of NaCNBH₄ was added with continuously stirring 270 nm after 1:9 methanol dissolution of fractions collected from the Sepharose column. A reference measurement was also taken of the OD at 450 nm without methanol dissolution. Then, the ratio of total amount of drug content in the liposome fractions to total drug fractions was calculated. In this example, the liposome particle size of 131.5 nm and a drug entrapment of 61% were obtained.

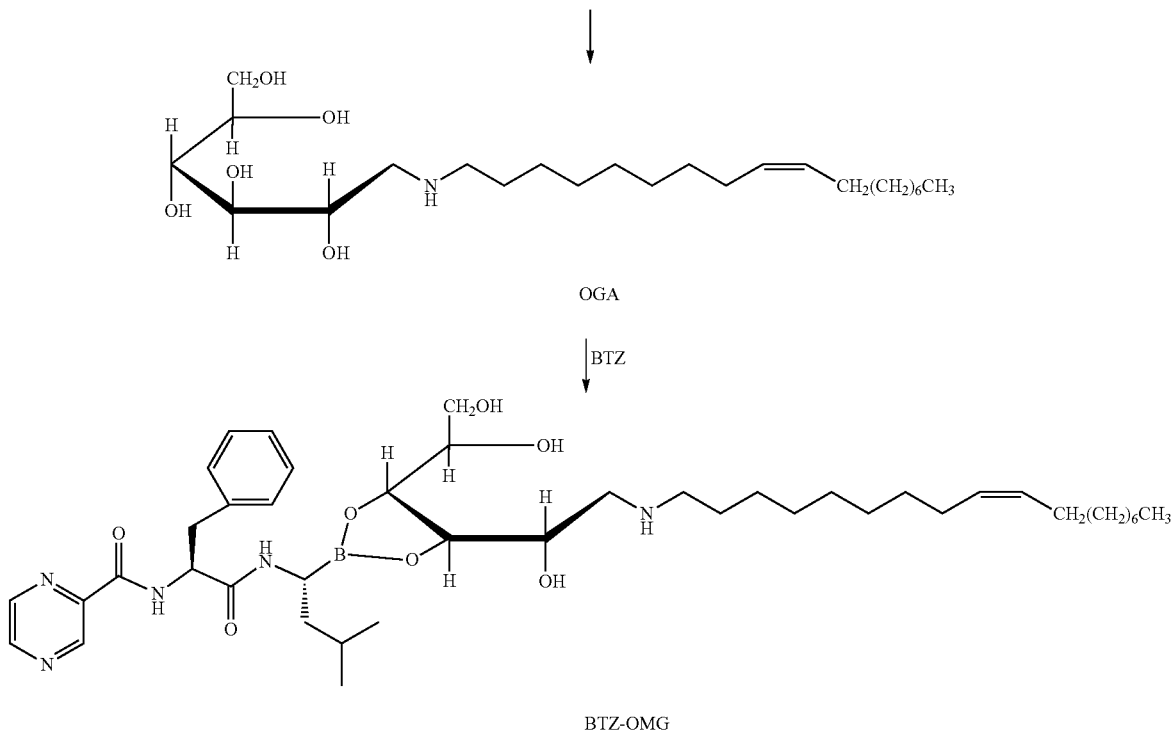

Scheme 2. Structure and synthesis of BTZ-OGA.

until the evolution of hydrogen subsided. The mixture was acidified to a pH of 2-3 by the dropwise addition of concentrated HCl. The product precipitated in the form of HCl salt was isolated by centrifugation and washed with ice water.

Preparation of a Liposomal Formulation of BTZ-OGA

Egg L-α-phosphatidylcholine (egg PC), cholesterol, 1,2-distearoyl-sn-glycero-3-phosphoethanolamine (DSPE) conjugated polyethylene glycol (PEG) (mPEG-DSPE), and BTZ-OGA were dissolved in chloroform at a molar ratio of 40:36:4:20. Rotary evaporation was applied to form a dry lipid film, followed by hydration with 50 mM sodium acetate buffer and 10% lactose at a pH of 8.5. Extrusion was used to reduce the liposome size to 150 nm or less. Any remaining unencapsulated drug was then removed through size exclusion chromatography on a Sepharose CL-4B column. Finally, the liposomes were sterile filtered and lyophilized.

Characterization of the Liposomal Formulation of BTZ-OGA

The liposome particle size distribution was determined through dynamic light scattering on a NICOMP Submicron Particle Sizer Model 370. The encapsulation efficiency was examined by a UV-visible spectrophotometer as the OD at Example 3. Preparation, Formulation, and Evaluation of BTZ-MEGA-12

A liposomal formulation based on MEGA-12 was also investigated. The structure of MEGA-12 and BTZ-MEGA-12, well as the strategy for preparing BTZ-MEGA-12, are shown in Scheme 3.

Synthesis of BTZ-MEGA-12

MEGA-12 and BTZ at 2:1 molar ratio were co-dissolved in tert-Butanol. Reaction was achieved by continuous stirring for overnight at room temperature.

Preparation of a Liposomal Formulation of BTZ-MEGA-12

Egg L-α-phosphatidylcholine (egg PC), cholesterol, 1,2-distearoyl-sn-glycero-3-phosphoethanolamine (DSPE) conjugated polyethylene glycol (PEG) (mPEG-DSPE), and BTZ-MEGA-12 were dissolved in chloroform at a molar ratio of 40:38:2:20. Rotary evaporation was applied to form a dry lipid film, followed by hydration with 50 mM sodium acetate solution and 5 mM sodium phosphate buffer with 10% lactose at a pH of 8. Extrusion was used to reduce the liposome size to 150 nm or less. Any remaining unencapsulated drug was then removed through size exclusion chromatography on a Sepharose CL-4B column. Finally, the liposomes were sterile filtered and lyophilized.

Optimization of Liposomal Loading

Figure 2:
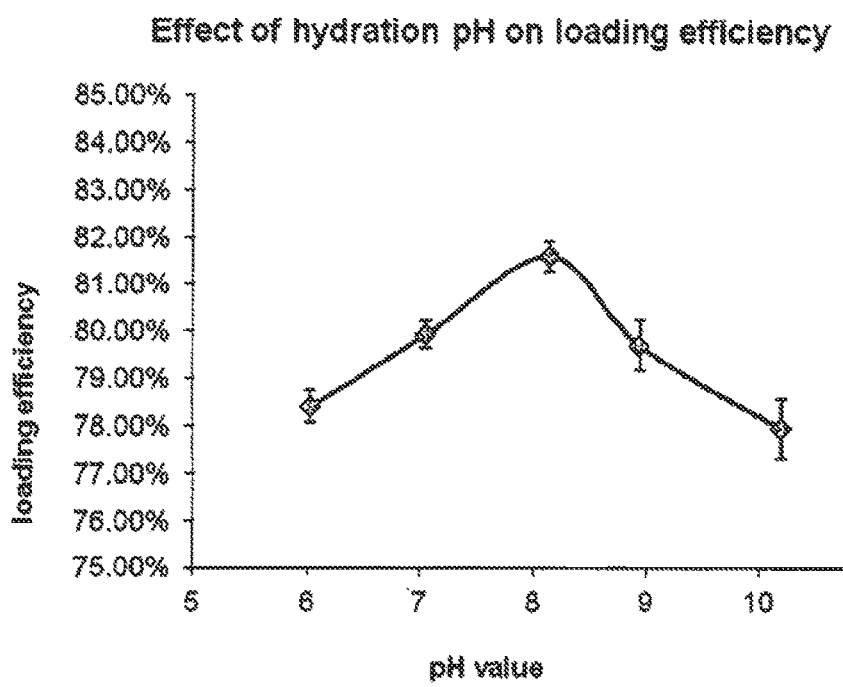
FIG. 2 is a graph illustrating the effect of pH on the loading efficiency of BTZ-MEGA-12 in liposomes.

The effect of hydration pH on loading efficiency for the MEGA-12 liposomal formulation was examined from pH 6 to pH 10 using 50 mM sodium acetate and 5 mM sodium phosphate as the hydration buffer. The results are plotted in FIG. 2. This study demonstrated that drug loading was maximized at pH 8. However, the pH dependency was limited, with the loading efficiency consistently in the range of 78%-82% at all pH's tested, with the highest loading of 81.6% at pH 8.

The encapsulation efficiency of BTZ-MEGA-12 in the liposomal formulation was investigated by UV-vis, according to the methods described above. The results show that a drug entrapment of ~81.6% was obtained.

Synthesis of BTZ-glucitol-DPPE

Glucitol-DPPE and BTZ at 2:1 molar ratio were stirred in chloroform/tert-butanol/$H_2O$ (5:4:1). Reaction was achieved by continuous stirring for overnight at room temperature.

Preparation of a Liposomal Formulation of BTZ-glucitol-DPPE

Egg PC, cholesterol, mPEG-DSPE, and BTZ-glucitol-DPPE were dissolved in chloroform at a molar ratio of 40:38:2:20. Rotary evaporation was applied to form a dry lipid film, followed by hydration with 50 mM sodium acetate solution and 10 mM glycine buffer with 10% lactose at a pH of 8.5. Extrusion was used to reduce the liposome

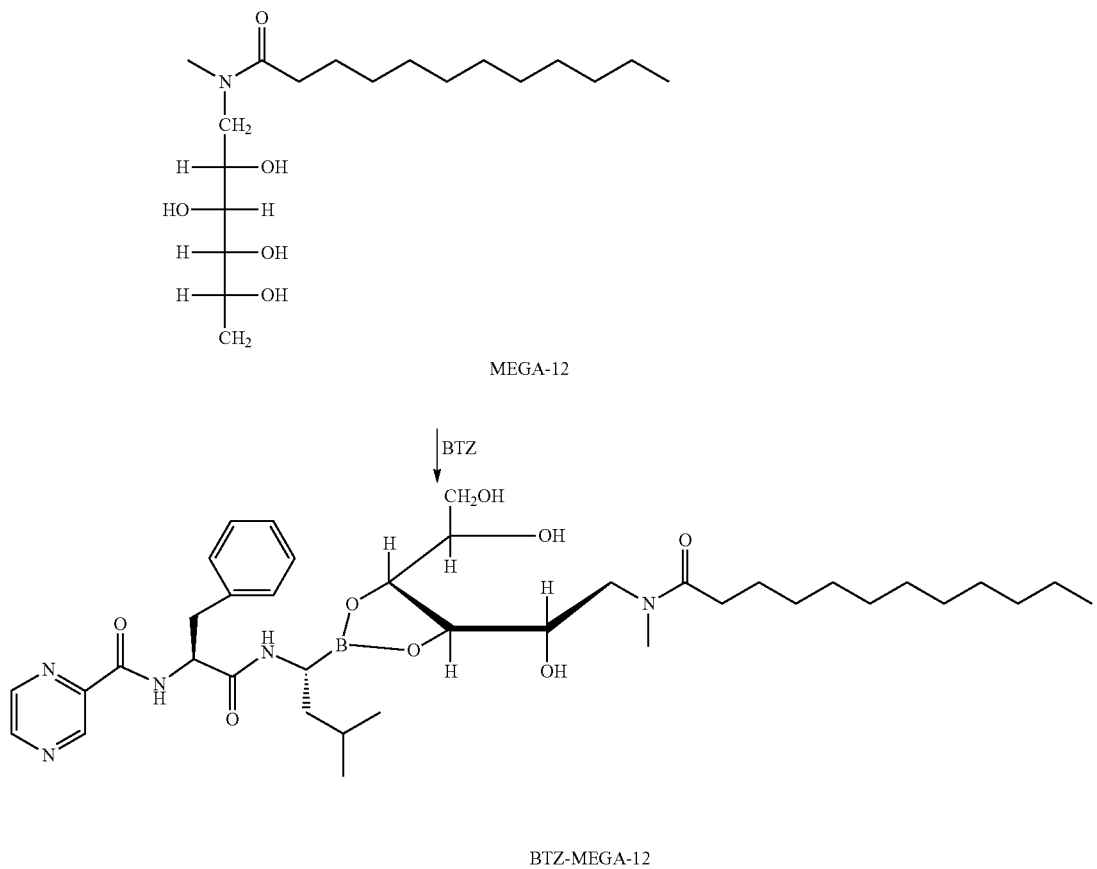

Scheme 3. Structure and synthesis of BTZ-MEGA-12.

Optimization of Liposomal Loading

The effect of hydration pH on loading efficiency for the MEGA-12 liposomal formulation was examined from pH 6 to pH 10 using 50 mM sodium acetate and 5 mM sodium phosphate as the hydration buffer. The results are plotted in FIG. 2. This study demonstrated that drug loading was maximized at pH 8. However, the pH dependency was limited, with the loading efficiency consistently in the range of 78%-82% at all pH's tested, with the highest loading of 81.6% at pH 8.

Figure 3:
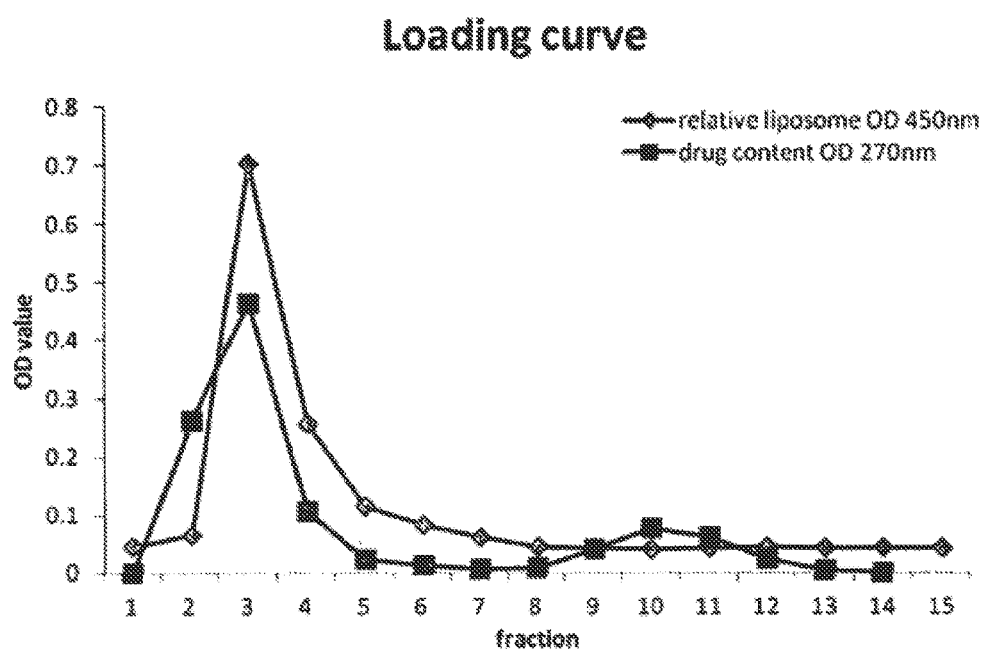
FIG. 3 is a Sepharose CL-4B chromatogram illustrating the loading of a liposomal formulation of BTZ-MEGA-12.

The encapsulation efficiency of BTZ-MEGA-12 in the liposomal formulation was investigated by UV-vis, according to the methods described above. The results show that a drug entrapment of up to 81.6% was obtained (FIG. 3).

Example 4. Preparation of BTZ-glucitol-DPPE

The structure of glucitol-DPPE and BTZ-glucitol-DPPE, as well as the strategy for preparing BTZ-glucitol-DPPE, are shown in Scheme 4.

size to 150 nm or less. Any remaining unencapsulated drug was then removed through size exclusion chromatography on a Sepharose CL-4B column. Finally, the liposomes were sterile filtered and lyophilized.

Characterization of the Liposomal Formulation

The liposome particle size distribution was determined through dynamic light scattering on a NICOMP Submicron Particle Sizer Model 370. The encapsulation efficiency was examined by a UV-visible spectrophotometer as the OD at 270 nm after 1:9 methanol dissolution of fractions from the Sepharose CL-4B column. A reference measurement was also taken of the OD at 450 nm without methanol extraction. Then, the ratio of total amount of drug content in the liposome fractions to total drug fractions was calculated. In this example, the liposome particle size of 97.3 nm was obtained.

Scheme 4. Structure and synthesis of BTZ-glucitol-DPPE.

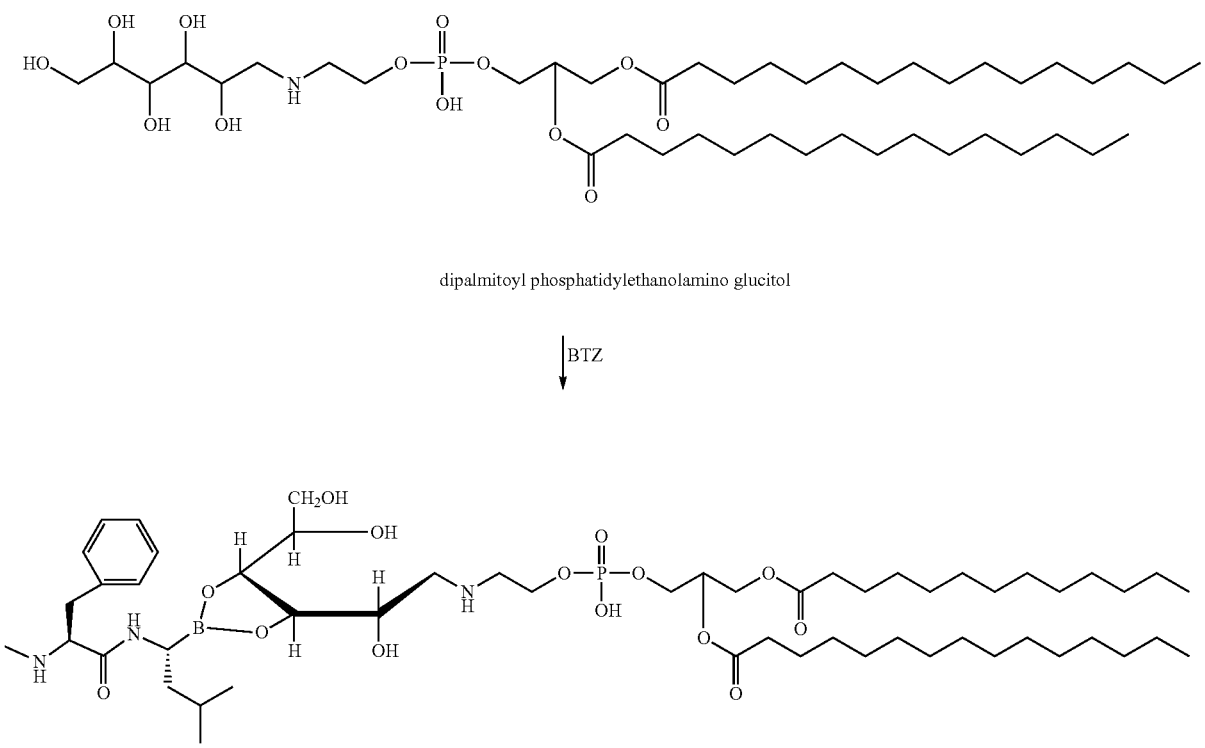

dipalmitoyl phosphatidylethanolamino glucitol

Example 5. Preparation, Formulation, and Evaluation of BTZ-MEGA-CHOL

The structure of 3β-[N-(methylglucamine)carbamoyl] cholesterol (MEGA-CHOL) and BTZ-MEGA-CHOL, as well as the strategy for preparing BTZ-MEGA-CHOL, are shown in Scheme 5.

Preparation of MEGA-CHOL

Cholesteryl chloroformate (2.70 g) and 9 mL CHCl$_3$ were added to a 25 mL round bottom flask. Next, meglumine (1.74 g) in 8 mL DMSO and triethylamine (240 μm) were added. The mixture was stirred at room temperature for 12 h. The reaction was monitored by TLC and HPLC. The mixture was then poured into water. The precipitate was filtered and washed with water to afford crude MEGA-CHOL as a colorless solid. The crude product was purified by column chromatography on silica gel with methanol and chloroform (1:2 v/v). The product was analyzed by thin-layer chromatography and had an R$_f$ of 0.50 (methanol: chloroform, 1:2, v/v). In addition, the product was characterized by $^1$H NMR (CDCl$_3$) and showed the following peaks: 0.68 (s, 2H, HC); 0.88-1.12 (m, 12H, —CH$_3$); 1.27 (s, 1H, HC (ring)); 1.63 (m, 12H, —CH$_2$(side chain)); 1.88-2.01 (m, 3H, HC (ring)); 2.35 (m, 2H, HC (ring)); 2.62 (s, 7H, meglumine H); 2.97 (s, 2H, CH$_2$), 3.82 (m, 6H, meglumine H); 4.48 (s, 1H, H—C—C—O), 5.39 (s, 1H, H—C=C). Finally, the product was also analyzed by HPLC (using a Thermo Finnigan Surveyor HPLC system).

Scheme 5. Structure and synthesis of BTZ-MEGA-CHOL.

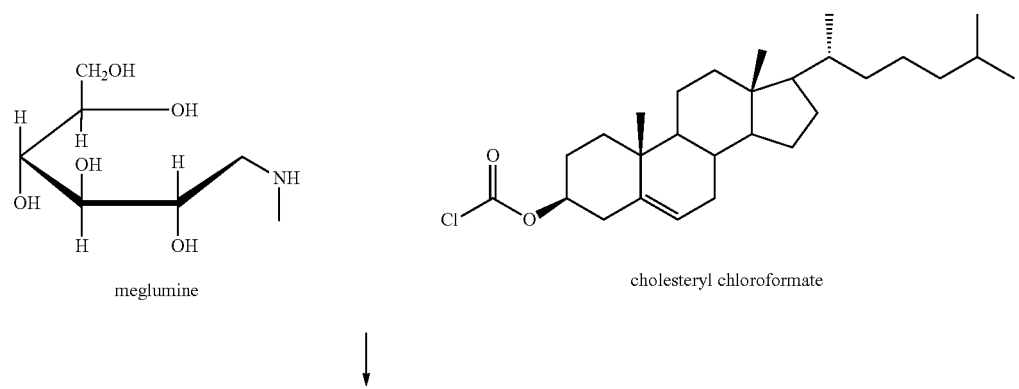

meglumine                cholesteryl chloroformate

-continued

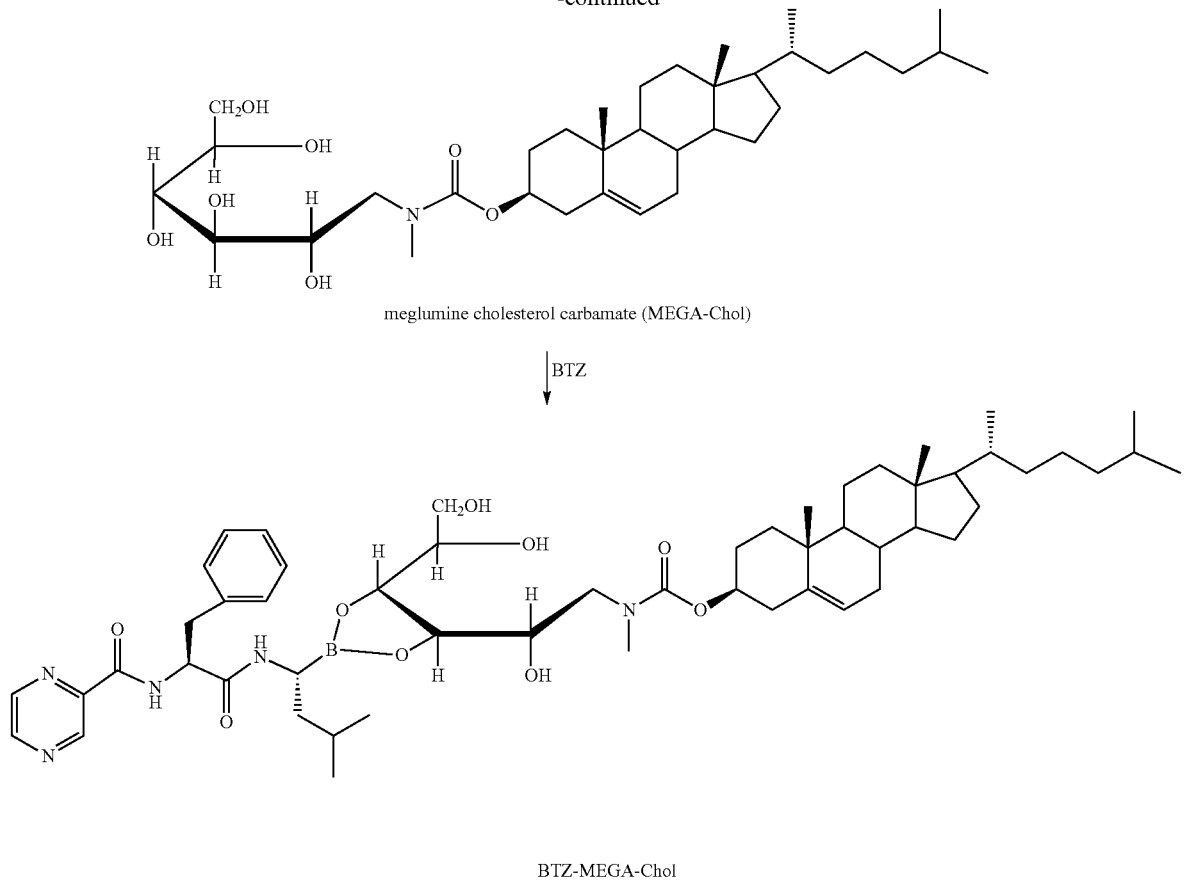

meglumine cholesterol carbamate (MEGA-Chol)

↓ BTZ

BTZ-MEGA-Chol

Preparation of BTZ-MEGA-CHOL

BTZ-MEGA-CHOL was prepared by combining BTZ with MEGA-CHOL in tert-butanol at room temperature, and lyophilizing the mixture. $^1$H NMR (CDCl$_3$): 0.68 (s, 6H, HC); 0.88-1.12 (m, 30H, —CH$_3$); 1.26-1.48 (s, 14H (alkyl BTZ)); 1.61 (m, 10H, —CH$_2$(side chain)); 1.84-2.43 (m, 10H, HC (ring)); 2.62 (s, 7H, meglumine H); 2.97 (s, 4H, CH2), 3.20 (s, 2H, BTZ benzene ring conjugated CH$_2$), 3.80-3.96 (m, 10H, meglumine H); 4.45 (s, 1 H, H—C—C—O), 5.37 (s, 1H, H—C=C), 7.20 (m, 5H, benzene ring, overlapped by CHCl$_3$ solvent peak), 8.54-9.35 (s, 3H, BTZ pyrazine ring).

Alternatively, BTZ-MEGA-CHOL was synthesized in chloroform using a 2× excess of MEGA-CHOL at room temperature, and incorporated into the liposomes in a continuous process. For the continuous process, BTZ and MEGA-CHOL at molar ratio of 1:2 were dissolved chloroform and incubated overnight at room temperature. The resulting complex, BTZ-MEGA-CHOL, was dissolved in chloroform with hydrogenated L-α-phosphatidylcholine (soy PC; HSPC), cholesterol, 1,2-distearoyl-sn-glycero-3-phosphoethanolamine (DSPE) conjugated polyethylene glycol (PEG$_{2000}$) (PEG$_{2000}$) (PEG$_{2000}$-DSPE), at a molar ratio of 20:40:36:4 at 50 mg/ml. Rotary evaporation was used to form a dry lipid turn in a round-bottom flask, followed by vacuum drying for another 2 hrs. Buffer containing 50 mM sodium acetate and 10 mM glycine at pH 8 was used to hydrate this film at a lipid concentration of 50 mg/ml. Sonication was then applied to reduce particle size to 200 nm or smaller. Next, sample was loaded on a Sepharose CL-4B column to remove free BTZ. Fractions containing L-BTZ were collected and 10% sucrose was added. This product was then filtered through a 0.22 μm membrane filter and lyophilized.

Figure 4:
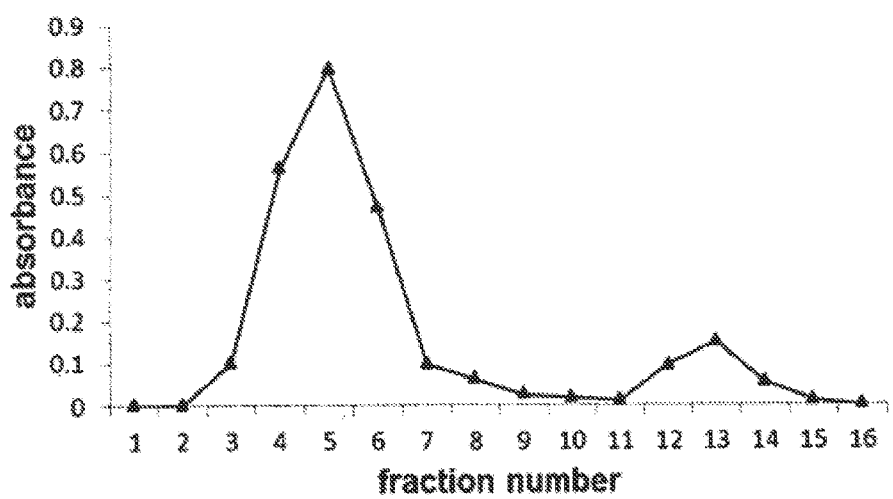
FIG. 4 is a Sepharose CL-4B chromatogram illustrating the loading of a liposomal formulation of BTZ-MEGA-CHOL.

The encapsulation efficiency of the drug was investigated by UV-vis, as described above. Specifically, the lyophilized prodrug BTZ-MEGA-CHOL was reconstituted in ddH$_2$O and loaded on a Sepharose CL-4B column and the eluate was collected at 1 mL per fraction. Each fraction was analyzed by UV-vis spectrophotometry. FIG. 4 displays the normalized results for BTZ-MEGA-CHOL (e.g., Y-axis is the absorbance of each fraction after the substraction of the absorbance values of the control). A drug entrapment efficiency of 80.11% was obtained.

Evaluation of Lyophilized Liposomal Formulations of BTZ-MEGA-CHOL

Figure 5:
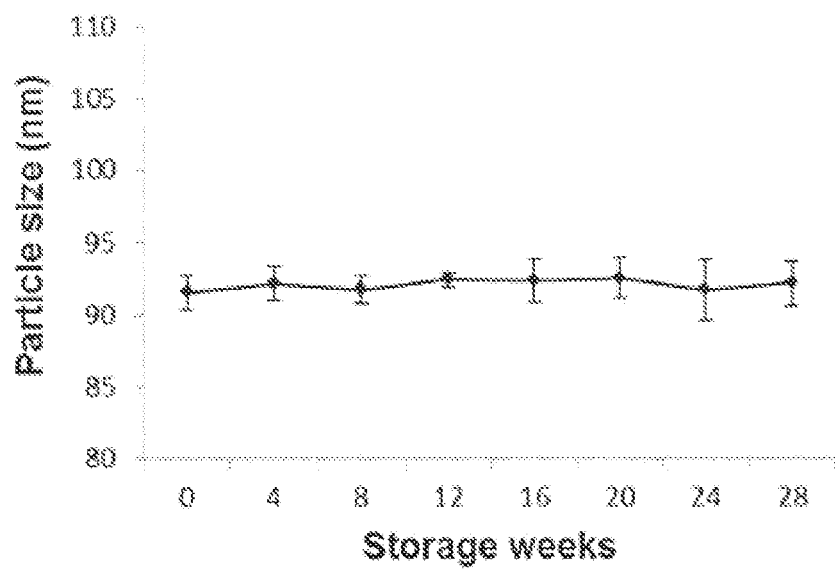
FIG. 5 is a plot showing the colloidal stability of a lyophilized liposomal formulation of BTZ-MEGA-CHOL over a period of 28 weeks.

The colloidal stability of lyophilized liposomal formulations of BTZ-MEGA-CHOL was evaluated. The lyophilized liposomal formulation of BTZ-MEGA-CHOL was stored at room temperature and monitored over time. At varying intervals over 28 weeks, the lyophilized liposomal formulation of BTZ-MEGA-CHOL was re-hydrated, and the particle size was measured as described above. The results are plotted in FIG. 5. The results shown are the mean of 3 separate experiments, and the error bars represent the standard deviation.

Figure 6:
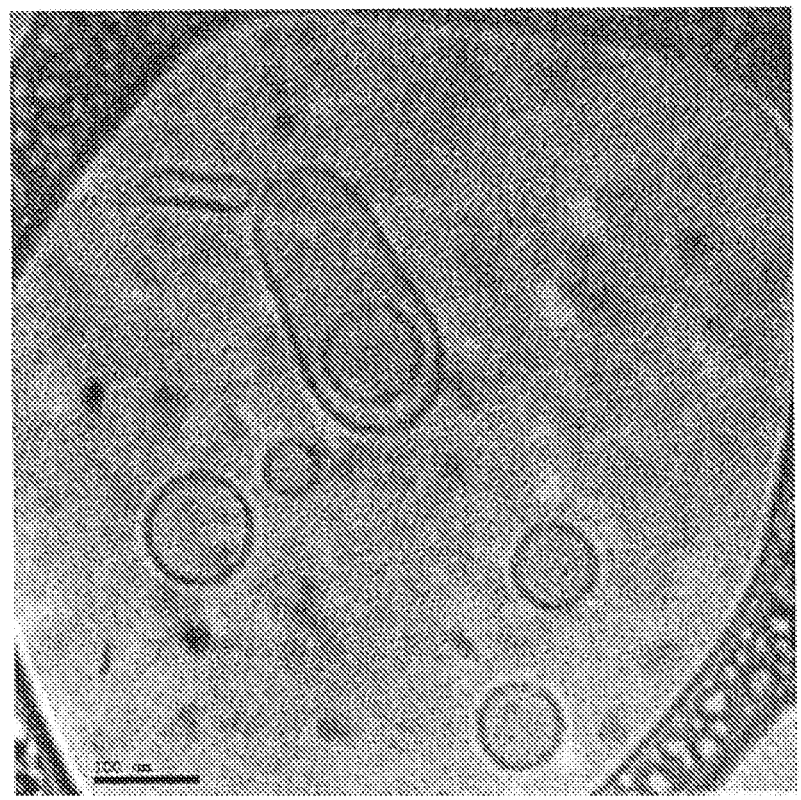
FIG. 6 is a cryo-TEM micrograph of a lyophilized liposome including BTZ-MEGA-CHOL.

The lyophilized liposomal formulation of BTZ-MEGA-CHOL was also evaluated by cryo-transmission electron microscopy (Cryo-TEM). One drop of sample containing lyophilized liposomes including BTZ-MEGA-CHOL was added to each glow-discharged holey carbon/formvar film coated grid in a controlled environment vitrification system at constant humidity and temperature of 25° C. The samples were blotted and vitrified by immediately plunging into a bath of liquid ethane slush. Prepared grids were stored under liquid nitrogen temperature until transferred to a Gatan cryo-holder operating at −172° C. and imaged in low-dose mode with an FEI Tecnai G2 Spirit TEM equipped with bioTWIN optics operating at 120 kV. Images were recorded using a Gatan CeD camera equipped with a post column Gatan energy filter (GIF) at an angle of (0). A cryo-TEM micrograph of a lyophilized liposome including BTZ-MEGA-CHOL is shown in FIG. 6. As can be seen the liposomes had a spherical structure and are mostly unilamellar. In addition, the particle size of the liposomes was mostly under 100 nm.

Cytotoxicity of BTZ-MEGA-CHOL

Figure 7:
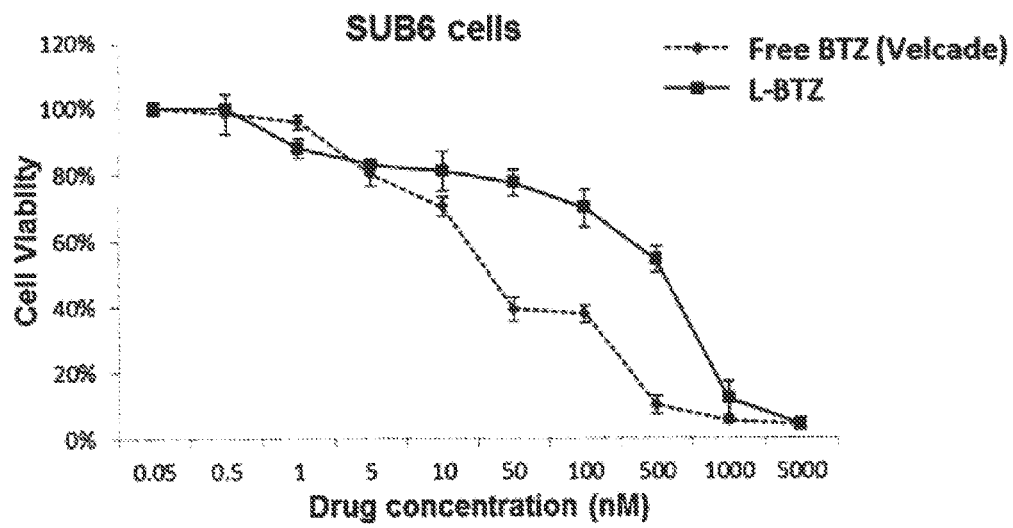
FIG. 7 is a graph showing the cytotoxicity of BTZ and BTZ-MEGA-CHOL to SUB6 leukemia cells.
Figure 8:
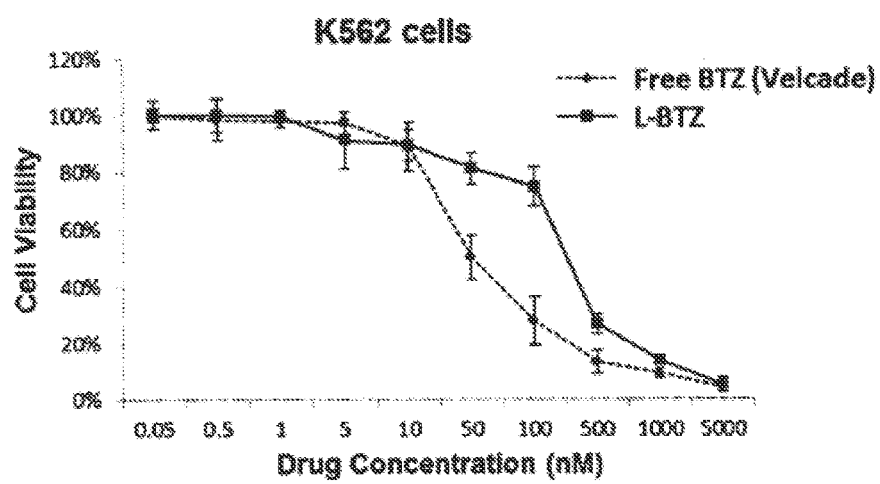
FIG. 8 is a graph showing the cytotoxicity of BTZ and BTZ-MEGA-CHOL to K562 leukemia cells.

Cell viability studies were performed using the liposomal formulation of BTZ-MEGA-CHOL on SUB6 cells (FIG. 7) and K562 cells (FIG. 8). Leukemia SUB6 and K562 cells were treated with diluted concentration of BTZ (VELCADE) or the liposomal formulation of BTZ-MEGA-CHOL for 48 hours in the range of 0.05-5000 nM. Cytotoxicity was measured using an MTS assay. The results shown in FIGS. 7 and 8 are the mean of 4 repeats, and the error bars represent the standard deviation. The results showed that liposomal BTZ was active against the leukemia cells but was less cytotoxic than the BTZ free drug. This is expected because BTZ needs to be released from the liposomes because being taken up by the cells. Liposomes are expected to be more active than the free drug in vivo due to their much longer circulation half-life.

In Vivo Studies of the Activity of BTZ-MEGA-CHOL

The therapeutic activity of BTZ-MEGA-CHOL was also investigated using animal studies. NSG mice were injected with $5 \times 10^5$ MV4-11 AML cells. The mice were divided into two groups of 10 each (Trial I), and were treated with empty liposomes or the liposomal formulation of BTZ-MEGA-CHOL at 1 mg/kg, twice a week, by tail vein injection. The study was repeated once with 5 mice in each group (Trial II). Three mice from each group were sacrificed after 4 weeks of treatment in Trial I for further analysis.

Figure 9:
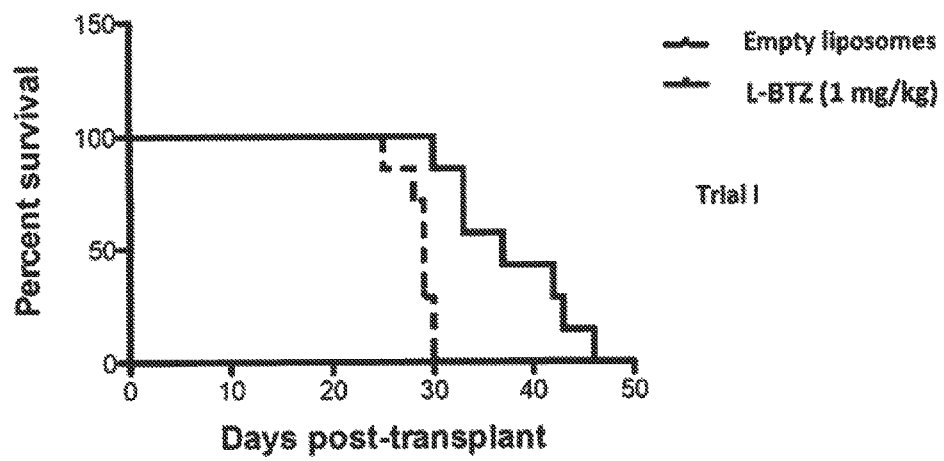
FIG. 9 is a graph of trial 1 evaluating the survival of MV4-11 engrafted NSG mice in response to treatment with a liposomal formulation of BTZ-MEGA-CHOL.
Figure 10:
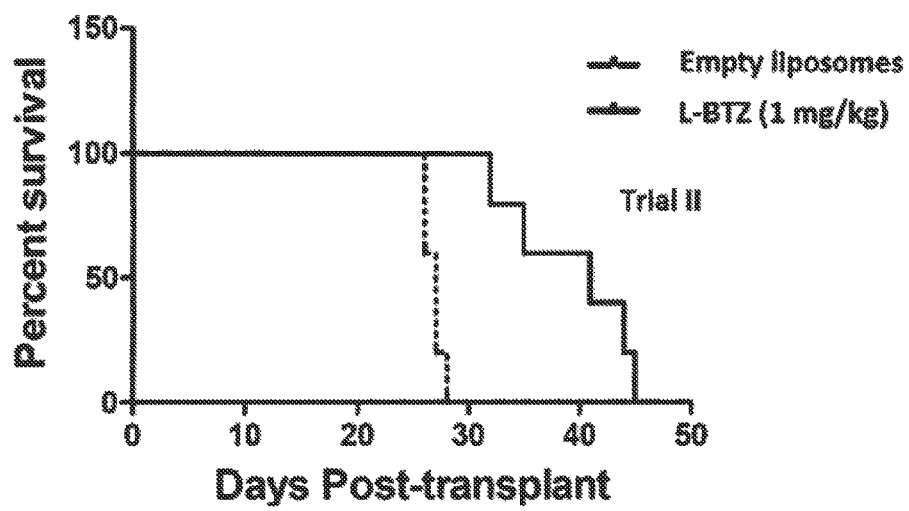
FIG. 10 is a graph of trial 2 evaluating the survival of MV4-11 engrafted NSG mice in response to treatment with a liposomal formulation of BTZ-MEGA-CHOL.
Figure 11:
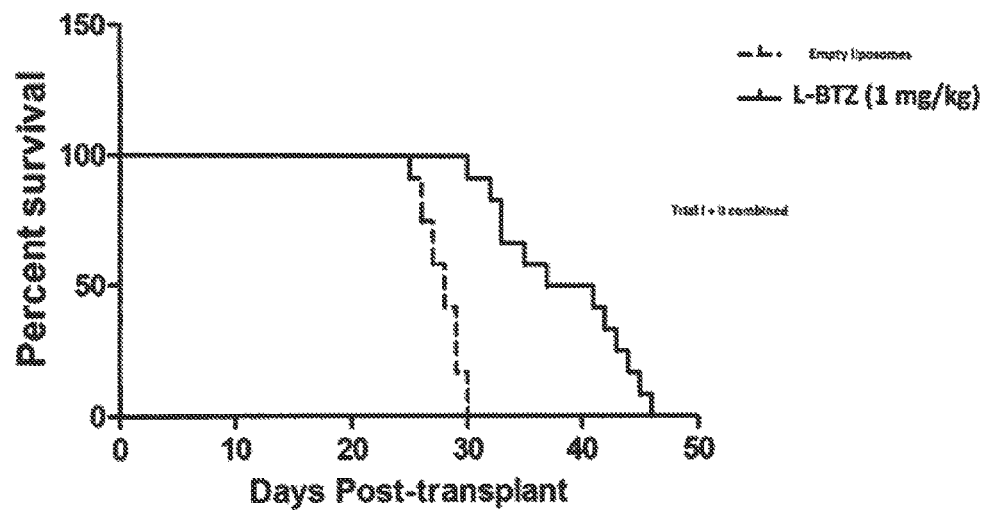
FIG. 11 is a graph of the combined results of trial 1 and trial 2 evaluating the survival of MV4-11 engrafted NSG mice in response to treatment with a liposomal formulation of BTZ-MEGA-CHOL.

Both trials showed a significant increase in survival of mice. For Trial I, the p value was 0.0007 (FIG. 9). For Trial II the p value was 0.0019 (FIG. 10). When the data set was viewed as a combination, the p value was <0.0001 and median survival of the mice was 28 days for the empty liposome treated (control) group and 39 days for the BTZ-MEGA-CHOL treated group (FIG. 11). These data collectively indicate the potent therapeutic activity of BTZ-MEGA-CHOL.

Figure 12:
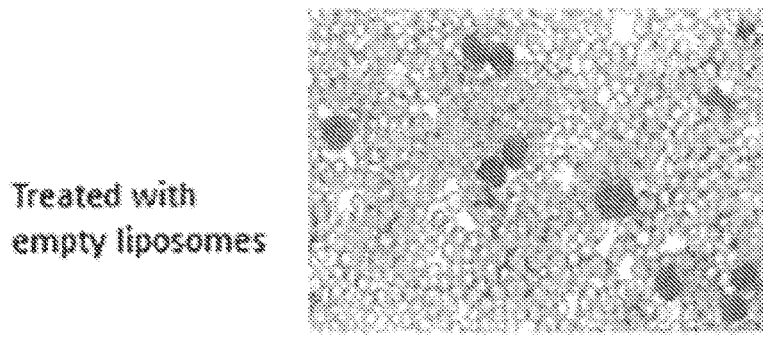
FIG. 12 are micrographs illustrating the difference in leukemic blast cell concentration in MV4-11 engrafted NSG mice following four weeks of treatment with empty liposomes (top micrograph) and four weeks of treatment with a liposomal formulation of BTZ-MEGA-CHOL (bottom micrograph). Treatment with a liposomal formulation of BTZ-MEGA-CHOL eliminated leukemic blast cells from the MV4-11 engrafted NSG mice after 4 weeks of treatment.
Figure 12:
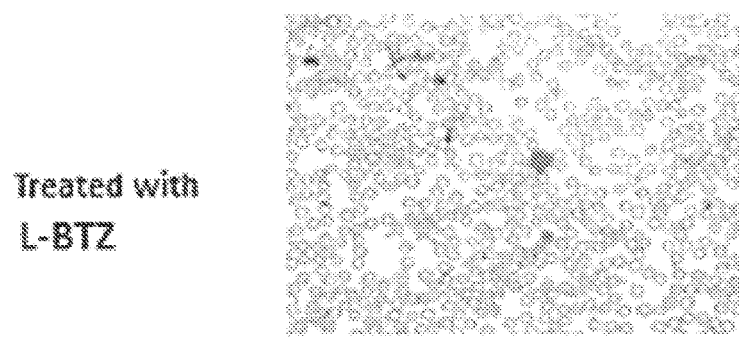
Figure 13:
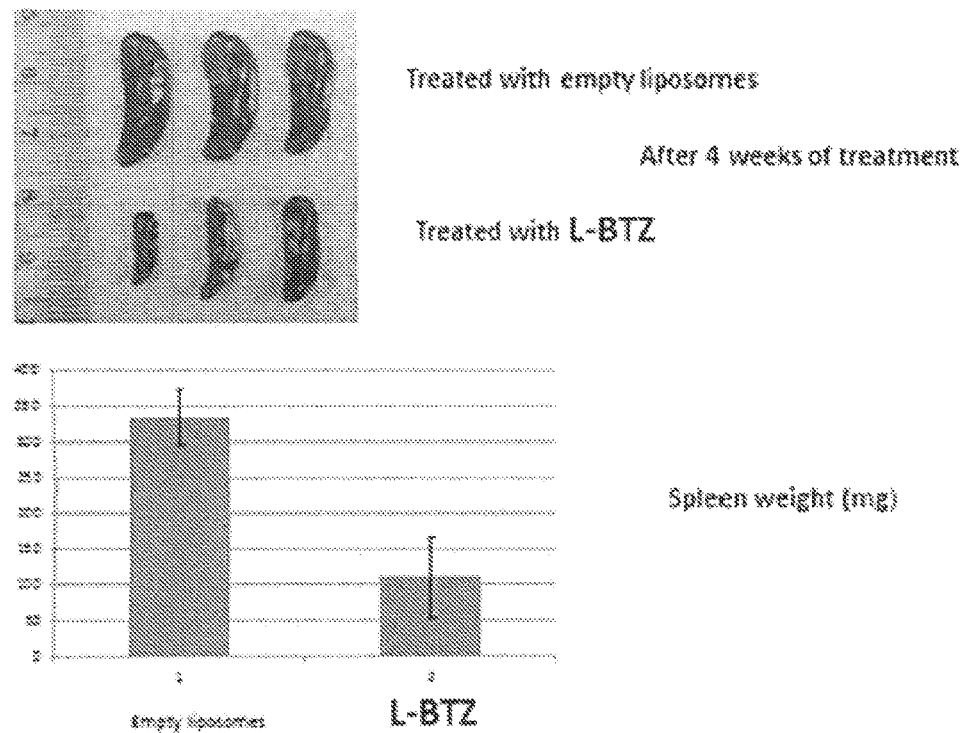
FIG. 13 illustrates that four weeks of treatment with a liposomal formulation of BTZ-MEGA-CHOL reduced the spleen size the MV4-11 engrafted NSG mice as compared to four weeks of treatment with empty liposomes.

6-8 week-old NSG mice (NOD.Cg-Prkdcscid Il2rgtm1Wjl/SzJ, The Jackson Laboratory, Bar Harbor, Me.) were intravenously (i.v.) injected through tail vein with $0.3 \times 10^6$ adapted MV4-11 cells. Both empty liposomes and L-BTZ were given for 4 weeks and then sacrificed. In the study, 3 mice per group were analyzed. Leukemic blast cells from peripheral blood of the mice from both of groups were analyzed by histological staining. In addition, the mice were evaluated spleen size and weight. The blood smear from both group were stained with Wright-Giemsa and the leukemic blast cells were visualized under the microscope. There was significant different in spleen size of L-BTZ treated group (FIG. 12). There were very few blast cells and the spleen was smaller compared with empty liposome treated group (FIG. 13).

Drug Release Studies

Figure 14:
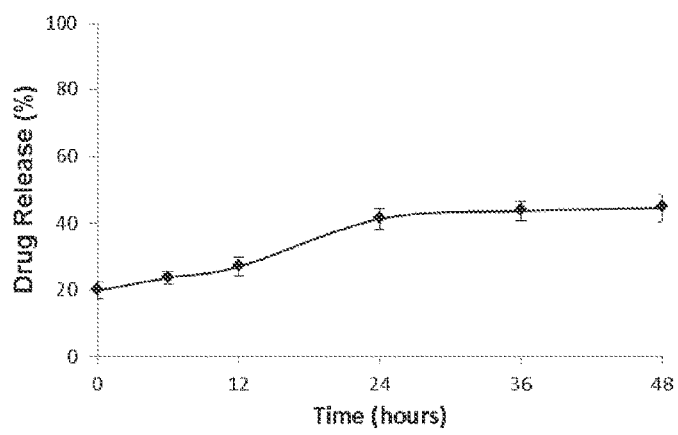
FIG. 14 is a graph that shows the rate of BTZ release from liposome by monitoring the drug content in liposomal over time in pH 7.4 phosphate-buffered saline (PBS) at 37° C.

The rate of BTZ release from BTZ prodrug was determined by monitoring the change in drug content in liposomes over time in pH 7.4 phosphate-buffered saline (PBS) at 37° C. L-BTZ (2 ml) was diluted by 18 mL of PBS with continuous stirring at 37° C. At various time intervals, 1 mL of sample was removed for analysis. Separation of L-BTZ from free BTZ was done by loading 1 mL of L-BTZ mixture through a 10 mL Sepharose CL-4B column at 1 mL per fraction equilibrated by water. Each fraction was then extracted by 9× methanol. After appropriate mixing, the concentrations of BTZ from each fraction were measured under UV spectrophotometer at OD 270 nm. The L-BTZ had already released 20% of the BTZ at the beginning of the experiment. The data (FIG. 14) shows that at pH 7.4 and 37° C. BTZ was slowly released from the liposome and a new equilibrium was reached at 40% free BTZ under the testing conditions. It is therefore concluded that L-BTZ should be reconstituted in water for injection at pH 8 and used within 8 hr of reconstitution and stored at ambient temperature or at 4° C.

Pharmacokinetic Studies

Figure 15:
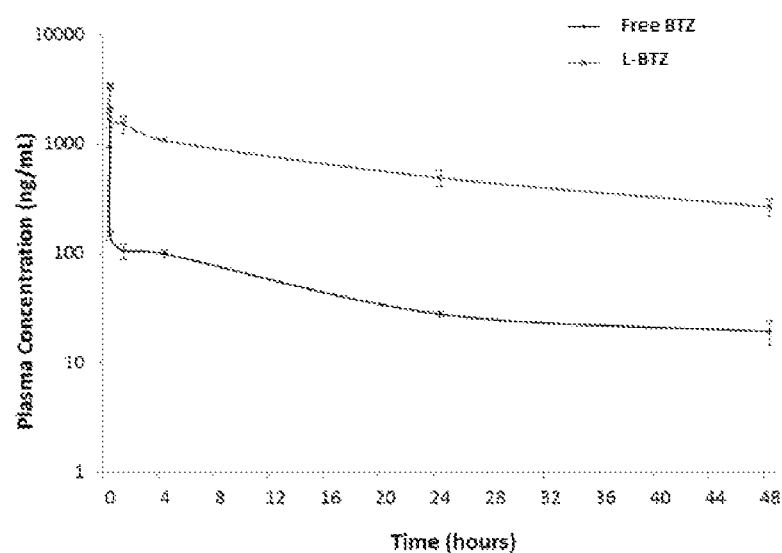
FIG. 15 is a graph that shows plasma drug concentration versus time in mice after i.v. administration of a single dose free BTZ and L-BIZ (1 mg/kg). Data are presented as the mean±SD (n=3).

The Pharmacokinetics of L-BTZ was studied in ICR mice (Charles River Lab, Wilmington, Mass.). The PK profile of free BTZ was also determined. Mice were given intravenous injections of free BTZ or L-BTZ at 1.0 mg/kg body weight via tail vein. At selected time intervals, a minimum of 100 μL blood plasma was collected from each mouse using heparin-containing tubes. Plasma was then isolated by centrifugation at 3000× g for 5 min. The drug concentration in plasma was determined by measuring Boron concentration through an inductively coupled plasma-optical emission spectrometer (ICP-OES). The Boron extraction and sample preparation has been described previously. The plasma concentration vs. time plot was shown in FIG. 15. The pharmacokinetic parameters of free BTZ and L-BTZ were calculated using WinNonlin software and a two-compartment model and are shown in Table 1.

TABLE 1

Pharmacokinetic parameters of free BTZ and L-BTZ in plasma after i.v. administration. Values are presented as the mean ± SD (n = 3).

|  | Free BTZ | L-BTZ |
| --- | --- | --- |
| $T_{1/2\alpha}$ (hr) | 0.10 ± 0.02 | 0.25 ± 0.10 |
| $T_{1/2\beta}$ (hr) | 18.26 ± 13.33 | 21.35 ± 3.80 |
| AUC (hr · μg/mL) | 2.87 ± 1.34 | 37.52 ± 3.87[a] |
| CL (mL/hr/kg) | 348.13 ± 162.69 | 26.65 ± 2.75 |
| $V_{ss}$ (L) | 7.46 ± 3.66 | 0.80 ± 0.12 |

[a]Statistically significance vs free BTZ (p < 0.05).

Limulus Amebocyte Lysate (LAL) Assay

L-BTZ was evaluated using a standard LAL assay. The results of the LAL assay are included in Table 2 below.

TABLE 2

Results of LAL Assay.

| | LAL Assay, EU/mg BTZ (% Spike Recovery) | |
| --- | --- | --- |
| Sample | Chromogenic | Turbidity |
| L-BTZ | 1746 (102) | 1060 (132) |
| Endotoxin Limit | 30.8 | 30.8 |

No microbial contamination was detected by an agar plate test. Measured endotoxin levels exceeded by approximately 30-60 times the suitable endotoxin limit.

Hydrodynamic Size and Zeta Potential

The hydrodynamic size of the liposomes in the L-BTZ formulation was measured using dynamic light scattering (low volume quartz cuvette, b=10 mm, 25° C., 633 nm laser, 173° scattering angle) upon 100 and 1000 fold dilution using two different dispersing media (10 mM NaCl and PBS buffer). The results are shown in Table 3 below.

TABLE 3

Dynamic Light Scattering Analysis the L-BTZ formulation upon 100 and 1000 fold dilution using two different dispersing media (10 mM NaCl and PBS buffer). Results are based on an average of 12 measurements.

| Dispersing Medium | Dilution | Z-Average (nm) | PdI | Int-Peak (nm) | % Int | Vol-Peak (nm) | % Vol |
|---|---|---|---|---|---|---|---|
| 10 mM NaCl | 100 | 95.7 (0.6) | 0.240 (0.007) | 131 (17) | 98 (2) | 73 (4) | 97 (3) |
| | 1000 | 101 (2) | 0.27 (0.02) | 141 (23) | 96 (4) | 79 (10) | 94 (6) |
| PBS Buffer | 100 | 101.5 (0.6) | 0.265 (0.006) | 152 (15) | 98 (5) | 86 (9) | 98 (4) |
| | 1000 | 103.1 (0.9) | 0.27 (0.01) | 150 (26) | 98 (2) | 78 (6) | 97 (4) |

These findings demonstrated that the liposomal particle size did not significantly change based on dilution or dispersing media.

The zeta potential of the liposomes in the L-BTZ formulation was also measured. A sample of L-BTZ was diluted 100 fold with 10 mM NaCl. The apparent zeta potential was then measured at 25° C. and a pH of 7.5. The liposomes had a negative zeta potential value of −16.1±0.3 mV.

Example 6. Protocol for the Preparation of BTZ-MEGA-CHOL at Mid-Scale (50 mg API BTZ)

A simple protocol was developed to prepare BTZ-MEGA-CHOL on a larger scale (e.g., on a 50 mg API BTZ scale).

Synthesis of Cholesterol-Meglumine Conjugate (MEGA-CHOL)

Cholesteryl chloroformate (351 mg) was dissolved in 9 mL $CHCl_3$ in a 25-mL round-bottom flask. Next, meglumine (102 mg) in 8 mL DMSO and triethylamine (73 µl) were added. The mixture was stirred at room temperature for 12 h. The reaction was monitored by TLC and HPLC. The mixture was poured into pure water. The precipitate was washed by 0.1N HCl to give a white crude product. This crude product was purified by column chromatography on silica gel with methanol and chloroform (1:2 v/v). $R_f$ 0.50 (methanol/chloroform, 1:2, v/v).

Preparation of Lipid-Drug Isopropanol Solution

BTZ and MEGA-CEOL (molar ratio 1:2) were dissolved in isopropanol and reacted for two hours. DSPC, cholesterol, and PEG-DSPE were then added into solution until they were completely dissolved. This solution was then diluted into 10 volumes of 20 mM phosphate buffer (pH=8) to form L-BTZ liposomes.

Homogenization Process

The above L-BTZ suspension was processed on a high-pressure homogenizer (Avestin Emulsiflex C5) at 10,000 psi with continuous processing to reduce the mean particle size to below 100 nm. And then the L-BTZ was filtered through 0.45 µm filter to remove any insoluble particles before tangential flow diafiltration (TFF).

TFF Process

The filtered L-BTZ was added into TFF system (Millipore Labscale TFF pump system used with a Midikros hollow fiber cartridge) and 5 mM phosphate buffer (pH=8) were used to wash L-BTZ with 5 volume replacements in order to remove isopropanol and free BTZ drug, and to concentrate the L-BTZ product.

Preparation of Final Liposomal Formulation

10% sucrose (cryoprotectant) was added into the liposomes after TFF. The final L-BTZ product was filtered through 0.22 µm PES membrane in biosafety cabinet and transferred into autoclaved glass vials and caps. The product was then stored at −70° C. until use.

The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A compound defined by Formula IA

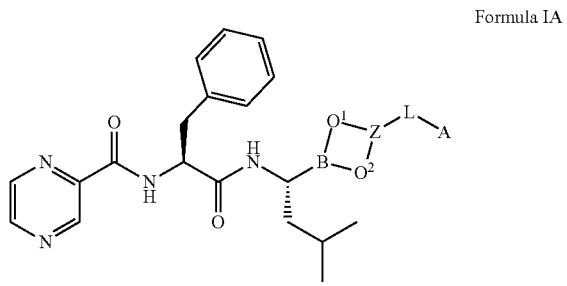

Formula IA wherein
 $Z$, together with $O^1$ and $O^2$, represent a moiety derived from a polyol, wherein the polyol comprises a sugar;
 L is absent, or is a linking group; and
 A comprises a lipid moiety chosen from a fatty acid, a glycerolipid, a phospholipid, a sphingolipid, a sterol, or a prenol.

2. The compound of claim 1, wherein the polyol comprises a monosaccharide.

3. The compound of claim 1, wherein the polyol comprises a reduced sugar.

4. The compound of claim 1, wherein the polyol comprises an amino sugar.

5. The compound of claim 1, wherein the polyol is meglumine, glucamine, mannitol, sorbitol, or fructose.

6. The compound of claim 1, wherein A is a $C_8$-$C_{40}$ alkyl group, a $C_8$-$C_{40}$ alkenyl group, a $C_8$-$C_{40}$ alkoxy group, a $C_8$-$C_{40}$ alkylthio group, a $C_8$-$C_{40}$ alkylsulfinyl group, a $C_8$-$C_{40}$ alkylsulfonyl group, a $C_8$-$C_{40}$ alkylamino group, a $C_8$-$C_{40}$ dialkylamino group, a $C_8$-$C_{40}$ alkylcarbonyl group, a $C_8$-$C_{40}$ alkoxycarbonyl group, a $C_8$-$C_{40}$ alkylaminocarbonyl group, a $C_8$-$C_{40}$ dialkylaminocarbonyl group, or a moiety defined by the formula below

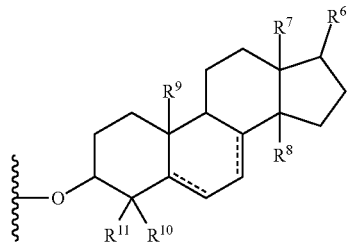

wherein
the dotted lines indicate that a single or double bond can be present;
$R^6$ is an alkyl group, an alkenyl group, an alkynyl group, an aryl group, an alkylaryl group, an arylalkyl group, a cycloalkyl group, an alkylcycloalkyl group, a heterocyclyl group, an alkylheterocyclyl group, a heteroaryl group, an alkylheteroaryl group, an alkoxy group, or an alkylthio group; and
$R^7$, $R^8$, $R^9$, $R^{10}$, and $R^{11}$ are, independently, hydrogen, a hydroxy group, an amino group, an alkyl group, an alkenyl group, an alkynyl group, an aryl group, an alkylaryl group, an arylalkyl group, a cycloalkyl group, an alkylcycloalkyl group, a heterocyclyl group, an alkylheterocyclyl group, a heteroaryl group, an alkylheteroaryl group, an alkoxy group, an alkylthio group, an alkylsulfinyl group, an alkylsulfonyl group, an alkylamino group, a dialkylamino group, an alkylcarbonyl group, an alkoxycarbonyl group, an alkylaminocarbonyl group, or a dialkylaminocarbonyl group.

7. The compound of claim 1, wherein the compound is defined by Formula IIA

Formula IIA

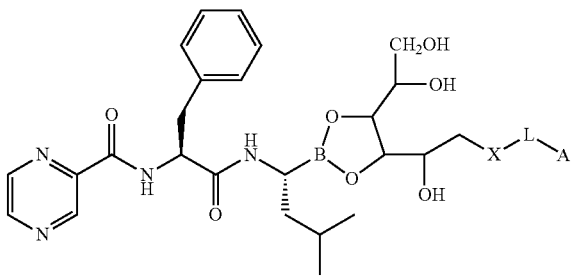

wherein
X is —O— or —$NR^{12}$—;
$R^{12}$ is hydrogen or an alkyl group,
L is absent or is a linking group; and
A comprises a lipid moiety chosen from a fatty acid, a glycerolipid, a phospholipid, a sphingolipid, a sterol, or a prenol.

8. The compound of claim 7, wherein X is —NH— or —N(CH$_3$)—.

9. The compound of claim 1, wherein the compound is

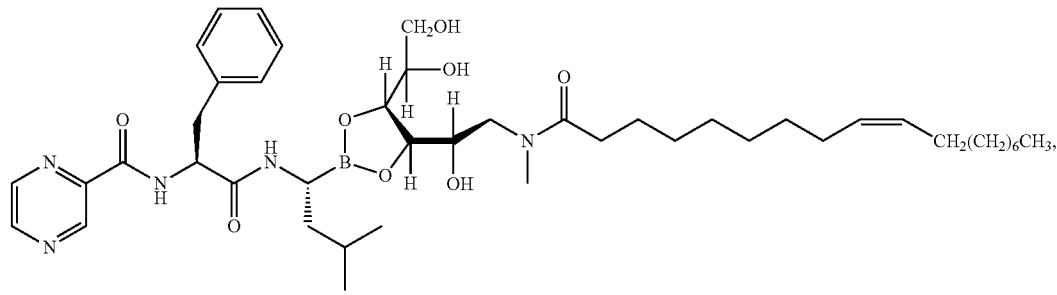

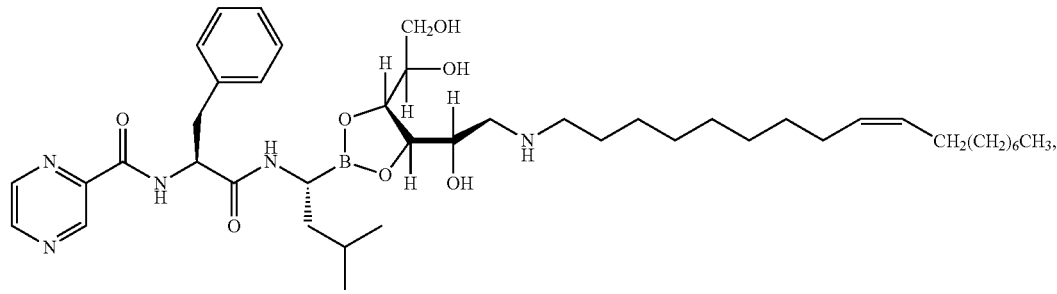

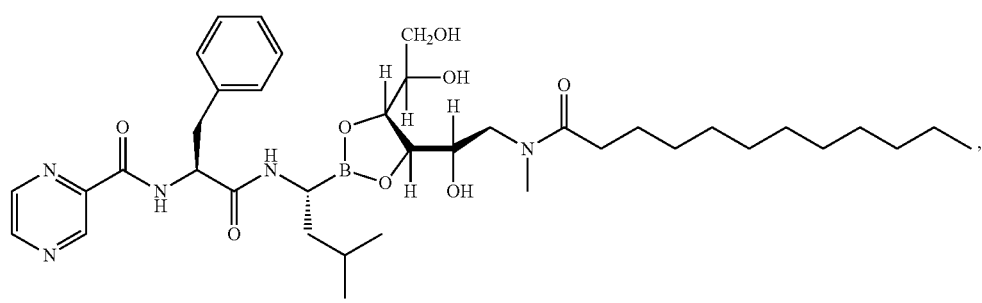

-continued

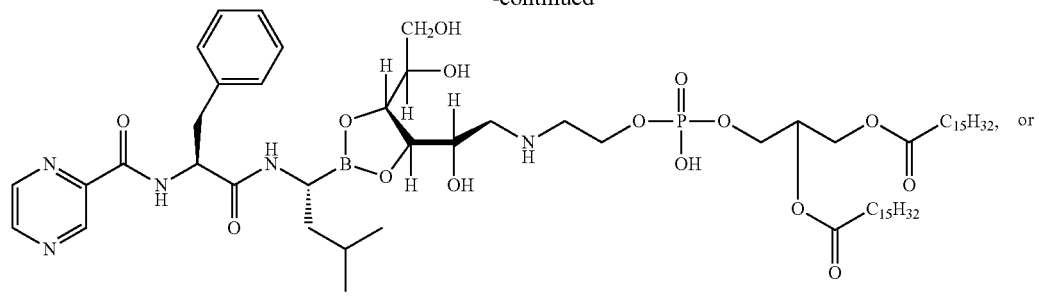

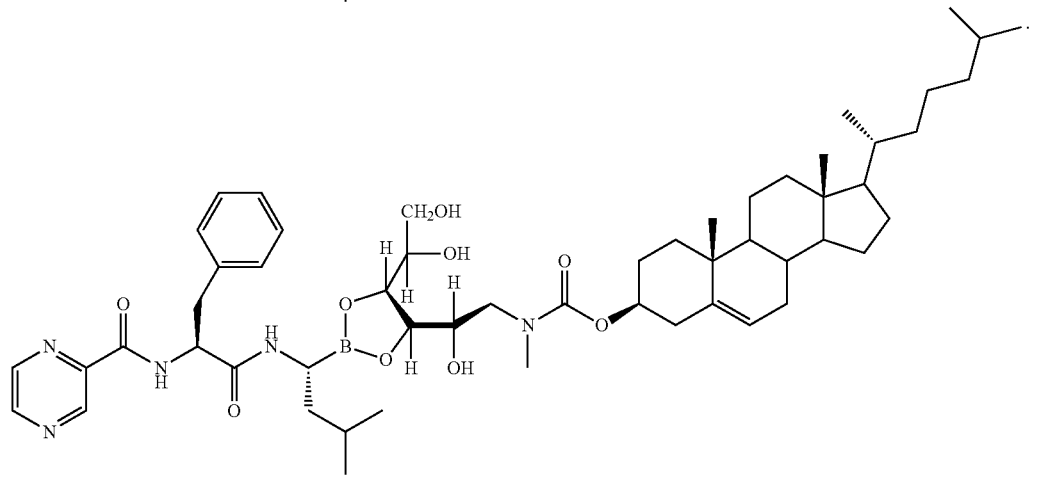

10. A pharmaceutical formulation comprising
(i) liposomes formed from a vesicle-forming lipid; and
(ii) a compound of claim 1 entrapped in the liposomes.

11. The formulation of claim 10, wherein the formulation is lyophilized.

12. The formulation of claim 10, wherein the formulation further comprises a lyoprotectant.

13. A method of treating cancer in a subject comprising administering to the subject a therapeutically effective amount of a compound defined by claim 1.

* * * * *